(12) United States Patent
Paterson et al.

(10) Patent No.: US 11,298,245 B2
(45) Date of Patent: Apr. 12, 2022

(54) METHOD FOR SURGICAL APPLICATION OF A GLENOID PROSTHESIS COMPONENT OF A SHOULDER JOINT PROSTHESIS AND RELATING SURGICAL INSTRUMENTS

(71) Applicant: LIMACORPORATE S.P.A., Villanova di San Daniele del Friuli (IT)

(72) Inventors: Paul Paterson, West Falls, NY (US); Michele Pressacco, Martignacco (IT); Andrea Fattori, Cividale del Friuli (IT); Marco Dosso, Udine (IT)

(73) Assignee: LIMACORPORATE S.P.A., Villanova di San Daniele del Friuli (IT)

( * ) Notice: Subject to any disclaimer, the term of this patent is extended or adjusted under 35 U.S.C. 154(b) by 102 days.

(21) Appl. No.: 15/872,303

(22) Filed: Jan. 16, 2018

(65) Prior Publication Data

US 2019/0216615 A1    Jul. 18, 2019

(51) Int. Cl.
| | | |
|---|---|---|
| *A61F 2/40* | (2006.01) |
| *A61F 2/30* | (2006.01) |
| *A61B 17/17* | (2006.01) |
| *A61F 2/46* | (2006.01) |
| *A61B 17/16* | (2006.01) |

(52) U.S. Cl.
CPC ............ *A61F 2/4612* (2013.01); *A61B 17/16* (2013.01); *A61F 2/30749* (2013.01); *A61F 2/40* (2013.01); *A61F 2/4059* (2013.01); *A61F 2/4081* (2013.01); *A61F 2/4601* (2013.01); *A61F 2/4014* (2013.01); *A61F 2002/30332* (2013.01); *A61F 2002/30405* (2013.01); *A61F 2002/30878* (2013.01); *A61F 2220/0008* (2013.01); *A61F 2220/0025* (2013.01)

(58) Field of Classification Search
CPC .............. A61B 17/155; A61B 17/1666; A61B 17/1746; A61B 34/20; A61B 5/4533; A61B 17/15; A61B 17/1668; A61B 17/025; A61B 17/17; A61B 17/1742; A61B 2017/1602; A61B 17/16; A61F 2/3859; A61F 2220/0025; A61F 2002/30507; A61F 2002/30761; A61F 2002/4677; A61F 2002/2825; A61F 2002/4018; A61F 2/32; A61F 2/3836; A61F 2002/30878; A61F 2/46; A61F 2/4081; A61F 2002/3085; A61F 2/30; A61F 2/4014; A61F 2/4612
See application file for complete search history.

(56) References Cited

U.S. PATENT DOCUMENTS 6,102,915 A * 8/2000 Bresler .................. A61F 2/4609
606/80
2001/0047210 A1* 11/2001 Wolf ..................... A61F 2/4612
623/19.14

(Continued)

*Primary Examiner* — Ann Schillinger
(74) *Attorney, Agent, or Firm* — Lucas & Mercanti, LLP

(57) ABSTRACT

The invention relates to a method for surgical application of a glenoid anchor of a shoulder joint prosthesis and instruments advantageously used in the method. The method includes making a delto-pectoral incision providing a delto-pectoral access to a shoulder joint; with the delto-pectoral access being suitable for inserting at least one machining tool; and making a trans-deltoid incision providing a trans-deltoid access to the humeral head; with the trans-deltoid access being suitable for inserting a stem of a machining instrument to be mounted on the machining tool for machining the glenoid cavity.

14 Claims, 31 Drawing Sheets

(56) References Cited

U.S. PATENT DOCUMENTS

| | | | |
|---|---|---|---|
| 2002/0095214 A1* | 7/2002 | Hyde, Jr. | A61F 2/4612 623/18.12 |
| 2003/0144738 A1* | 7/2003 | Rogalski | A61B 17/1778 623/19.11 |
| 2005/0043805 A1* | 2/2005 | Chudik | A61B 17/1778 623/19.14 |
| 2009/0270993 A1* | 10/2009 | Maisonneuve | A61B 17/1684 623/19.14 |
| 2015/0223941 A1* | 8/2015 | Lang | A61F 2/30942 623/19.11 |

* cited by examiner

METHOD FOR SURGICAL APPLICATION OF A GLENOID PROSTHESIS COMPONENT OF A SHOULDER JOINT PROSTHESIS AND RELATING SURGICAL INSTRUMENTS

DESCRIPTION

The present invention relates to a method for surgical application of a glenoid prosthesis component, in particular, a glenoid anchor of a glenoid prosthesis component.

The principles of the present invention are applicable to different types of shoulder joint prostheses with different types of glenoid components, but the description which follows is provided with more specific reference to an anatomical shoulder prosthesis having a glenoid component comprising a glenoid anchor and a bearing fixed on it, without this however implying any limitation of the Applicant's rights.

The present invention also relates to a retractor instrument suitable for keeping a predetermined glenohumeral clearance between a humeral head and a glenoid cavity of a shoulder blade; said retractor instrument is suitable for being advantageously used in the method according to present invention. It does not exclude the application of the retractor instrument in the surgery of other joints such as hip, knee, spinal column, etc., for keeping spaced the bone extremities of the articulation.

The present invention also relates to a cannulated guide retractor suitable for guiding insertion of a surgical instrument through an incision into a bone hole made into the bone. Said cannulated guide retractor could be advantageously used in the method according to present invention.

The present invention also relates to a cannulated machining tool suitable for machining a glenoid cavity; said cannulated machining tool could be advantageously used in the method according to present invention.

It does not exclude the application of the cannulated machining tool to other areas of the skeleton not limited to the example of the glenoid cavity.

FIELD OF APPLICATION

FIG. 1 shows a diagrammatic front view of bones comprised in a shoulder joint 100, also known as glenohumeral joint.

The shoulder joint 100 is a ball and socket joint between the glenoid cavity 102 of the scapula 101 and the top 103a of the head 103 of the humerus 104. Both the humeral head top and the glenoid cavity are covered by an articular cartilage that protects the bone during the movement.

The scapula also comprising two bones that protrude laterally above the glenoid: the acromion 108 and the coracoid process 106.

The shoulder joint is mainly stabilized by muscles and tendons of the rotator cuff. Said muscles are in particular, the supraspinatus, infraspinatus, teres minor and subscapularis, that hold the head of the humerus in the glenoid cavity during movement.

In particular, the subscapularis muscle allows the internal rotation and adduction of the head of the humerus and when the arm is raised, it draws the humerus forward and downward. It provides a powerful defense to the front of the shoulder-joint, preventing displacement of the head of the humerus.

Over and above these anatomical details, for the purposes of the present invention, it should be pointed out that the glenohumeral joint can be affected by pathological conditions that compromise the joint congruency with an alteration of the stability and the biomechanics associated with acute pain.

However, these problems may be solved surgically by attempting to restore the stability and biomechanics of the articulation so as to eliminate the pain from which the patient is suffering. In the clinical practice, the surgery is a shoulder joint replacement, known as arthroplasty, consisting in the implant of a shoulder prosthesis, such as a reverse or anatomical total prosthesis, as appropriate.

The total prosthesis normally comprises both a humeral prosthetic component and a glenoid component and, in so-called reverse prostheses, these components are substantially reversed compared to an anatomical total prosthesis.

The humeral component is designed to be fixed to the top of the humerus by means of a fixing stem inserted inside the humerus itself and the glenoid component is fixed to the glenoid cavity of the scapula.

Regarding the anatomical prosthesis, the glenoid component usually comprises a glenoid anchor; when fixed through biologic fixation, said glenoid component is also known as metal-back, with a conical pin portion protruding from a metal baseplate. The metal baseplate has also through holes for being fastened to the glenoid cavity by means of bone screws. A bearing of synthetic material, normally polyethylene, is affixed on the baseplate and engages with the humeral component.

Alternatively, for cemented and/or hybrid fixations, the glenoid anchor baseplate could be either entirely made in synthetic material itself and directly engage the humeral component through pins or keels protruding from the baseplate that are cemented into the bone, or present at least one metal protrusion which allows for biologic fixation.

PRIOR ART

The common shoulder replacement surgery consists in partially removing the damaged parts of humeral head and glenoid and replacing them with corresponding humeral prosthesis component and glenoid prosthesis component.

The surgical technique starts providing adequate access and visualization of the joint. Usually the access is a delto-pectoral access, that is provided starting from a skin incision located substantially frontally to the patient shoulder. Alternatively, a trans-deltoid access could be provided by the surgeon for the implant of the prosthesis.

Because the contact between the scapula and the humeral head is achieved in a plane parallel to the sagittal plane of the patient, the surgeon cannot visualize the contact surfaces of the glenoid cavity and the humeral head top.

Thus, in order to remove the damaged parts, shape the bone and fix the prosthesis components to the bone, the surgeon needs to expose the humeral head top and the glenoid cavity through the incision.

Although advantageous in various respects and substantially meeting needs, the surgical technique described above has a major drawback relating to the invasiveness due to the exposure of the glenoid cavity.

To expose the joint contact surfaces through the frontal incision, the surgeon needs to release muscles and ligaments that physiologically prevent the joint dislocation. In particular, the exposure of the glenoid cavity needs to release, inter alia, the subscapularis muscle.

When the implant of the shoulder prosthesis is completed the surgeon restores the tissues continuity with sutures.

As an expert well known, the duration and the quality of the post-surgery convalescence of the patient is directly proportional to the invasiveness of the surgery. In other word, more tissues are chopped off or damaged during the surgery, more will be the time that the surgery injuries take to completely heal, and the pain endured by the patient.

If the subscapularis is released during the surgery to expose the glenoid cavity, the function of said important muscle will be compromised until the tendon that connect the muscle to the bone is not completely healed. With the risk that said muscle does not heal well compromising forever its functionality and increasing the probability of implant failure.

The present invention aims to overcome these drawbacks by considering the technical problem of how to provide instruments and corresponding surgical method able to allow the implant of the glenoid component of shoulder joint prosthesis in a less invasive manner compared to the known solutions, while insuring the preservation of the subscapularis muscle.

SUMMARY OF THE INVENTION

The proposed solution forming the basis of the present invention is that of providing both a delto-pectoral access and a lateral or trans-deltoid access for the insertion of surgical instruments used for shaping the bone of the glenoid cavity and implanting the glenoid anchor. The surgical instruments advantageously comprise a tool to be inserted through the delto-pectoral access and a stem to be inserted through the lateral access for coupling the machining tool.

Unlike the known surgery methods for implanting a shoulder joint prosthesis, the method according to the present invention does not envisage the full glenoid cavity exposition.

On the basis of this proposed solution a first embodiment of the invention is provided by a method for surgical application of a glenoid anchor or a glenoid prosthesis component of a shoulder joint prosthesis, of the type comprising the steps of:
  making a delto-pectoral incision providing a delto-pectoral access to a shoulder joint comprising a humeral head of a humerus facing a glenoid cavity of a shoulder blade; the delto-pectoral access being suitable for inserting at least one machining tool;
  making a trans-deltoid incision providing a trans-deltoid access to the humeral head; the trans-deltoid access being suitable for inserting a stem of a machining instrument to be mounted on the machining tool for machining the glenoid cavity.

Preferably the delto-pectoral access is provided as first. It does not exclude that the surgeon could decide to provide the trans-deltoid access before providing the delto-pectoral access.

Advantageously, the method further comprises the steps of:
  exposing the humeral head;
  making a through trans-humeral hole into the humeral head extending in medio-lateral direction;
  returning the humeral head facing the glenoid cavity;
  providing a retractor instrument introduced through the delto-pectoral access for keeping a predetermined glenohumeral clearance between the humeral head and the glenoid cavity; the retractor instrument having at least an abutting element at least partially abutting against the humeral head and the shoulder blade keeping free the trans-humeral hole and the glenoid cavity;
  providing at least one machining tool in the glenohumeral clearance introduced through the delto-pectoral access;
  introducing a stem of a machining instrument through the trans-deltoid access and then the trans-humeral hole until a stem free end of the stem reaches the glenohumeral clearance;
  mounting at least one machining tool on the stem free end for machining the glenoid cavity. The method could further comprise a step of resecting the humeral head top. The humeral head top is preferably resected along a plane angled with respect to the transversal plane and defining a resection surface lying on the coronal plane.

The resected humeral head top could be advantageously used to provide a bone graft for at least partially fill the trans-humeral hole preferably at the end of the prosthesis implant in order to at least partially restore the bone continuity. Before the step of inserting a stem of a machining instrument through the trans-deltoid access, a cannulated guide retractor could be introduced through the trans-deltoid access. The cannulated guide retractor preferably has an instrument guide passage therethrough connecting the trans-deltoid access to the trans-humeral hole.

The insertion of the machining instrument stem through the trans-humeral hole is achieved introducing the stem through the instrument guide passage of the cannulated guide retractor.

Preferably, the cannulated guide retractor further comprises a retracting portion for retracting soft tissues located between the trans-deltoid incision and the trans-humeral hole.

Advantageously, the machining tool could have a longitudinal tool passage therethrough for inserting a guidewire introduced through the trans-deltoid access until a guidewire tip is inserted into the glenoid cavity. Then the introduction of the machining instrument stem could be guided by the previously implanted guidewire. In this way, the machining tool acts as a centering device for the insertion of the guidewire in a predetermined point on to the glenoid cavity.

The machining tool could also comprise a radial recess extending from a side of the machining tool to the tool passage. The radial recess advantageously allows to insert/extract the guidewire into/from the through passage of the machining tool or place/extract the through passage of the machining tool around/from the guidewire, while the guidewire is inserted into the glenoid cavity.

In this way, it is possible to use a plurality of machining tools to perform different machining jobs on the glenoid cavity exchanging tool without each time remove and replace the guidewire.

The method could also comprise the implant of a glenoid anchor, inserted through the delto-pectoral access, of the type having a peg extending from a baseplate. To implant said glenoid anchor it is advantageously used an impactor comprising an impactor stem inserted through the trans-deltoid access coupled to an impactor head inserted through the delto-pectoral access.

If the glenoid anchor is of the type having separated peg and baseplate to be coupled by interference fitting, the method advantageously provides an impactor with a passage therethrough for the insertion of a tightening rod with a threaded end tightened into the peg.

Another embodiment of the present invention relates to a retractor instrument suitable for keeping a predetermined glenohumeral clearance between a humeral head top of a humeral head and a glenoid cavity of a shoulder blade; the retractor instrument advantageously comprises a first abutting element adapted to at least partially abut against the humeral head keeping free the humeral head top and a second abutting element adapted to at least partially abut against the shoulder blade keeping free the glenoid cavity.

A further embodiment of the invention relates to a cannulated guide retractor suitable for guiding the insertion of a surgical instrument through an incision into a bone hole made into the bone; the cannulated guide retractor advantageously having a cannulated guide retractor passage therethrough that connect the incision to the bone hole.

The cannulated guide retractor preferably comprising an inserting portion adapted to be at least partially inserted into the bone hole and a retracting portion adapted to retract soft tissues between the incision and the bone.

A further embodiment of the invention relates to a cannulated machining tool suitable for machining a glenoid cavity of a shoulder blade, for example in a shoulder prosthesis implant; the cannulated machining tool could comprise a longitudinal passage therethrough adapted to be passed through by a guidewire for guiding the insertion a machining stem.

The cannulated machining tool could also advantageously comprise a radial recess extending from a side of the cannulated machining tool to the longitudinal passage for placing the longitudinal passage around the guidewire and/or extracting the cannulated machining tool from the guidewire when the guidewire is inserted into the bone.

Features and advantages of the surgery method and the associated instruments according to the invention will emerge from the description of a non-limiting example of embodiment provided with reference to the accompanying drawings.

DETAILED DESCRIPTION

As already mentioned above, the method and the instruments according to the present invention, which will be described in detail below, are applicable to implant a glenoid anchor or glenoid component of a shoulder joint prosthesis, which could be whatever type of shoulder joint prostheses with whatever type of glenoid component. In particular, it does not exclude the application of the method and the instruments of the present invention to the implant of a reverse shoulder prosthesis. Furthermore, each instrument according to the present invention could be used in the surgery of other joints such as hip, knee, spinal column, etc.

However, the method and the instruments are described below with reference to the implant of a glenoid component of an anatomical total shoulder prosthesis, such as that one shown in FIG. 18, having a glenoid component comprising a glenoid anchor and a bearing fixed on it, but only by way of a non-limiting example and for the purpose of simplification of description of the invention.

Figure 1:
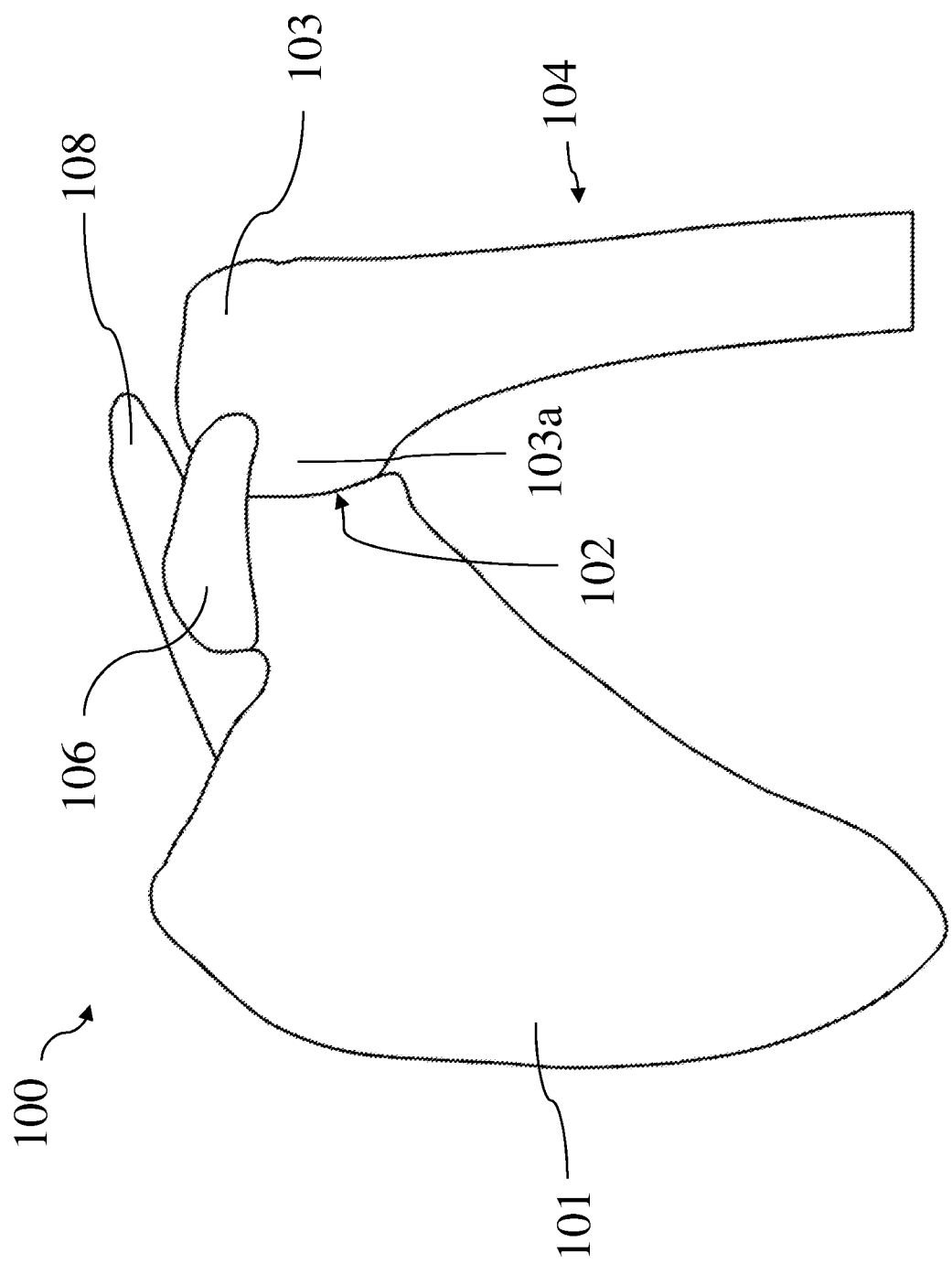
FIG. 1 shows a diagrammatic front view of the bones of a shoulder.
Figure 18:
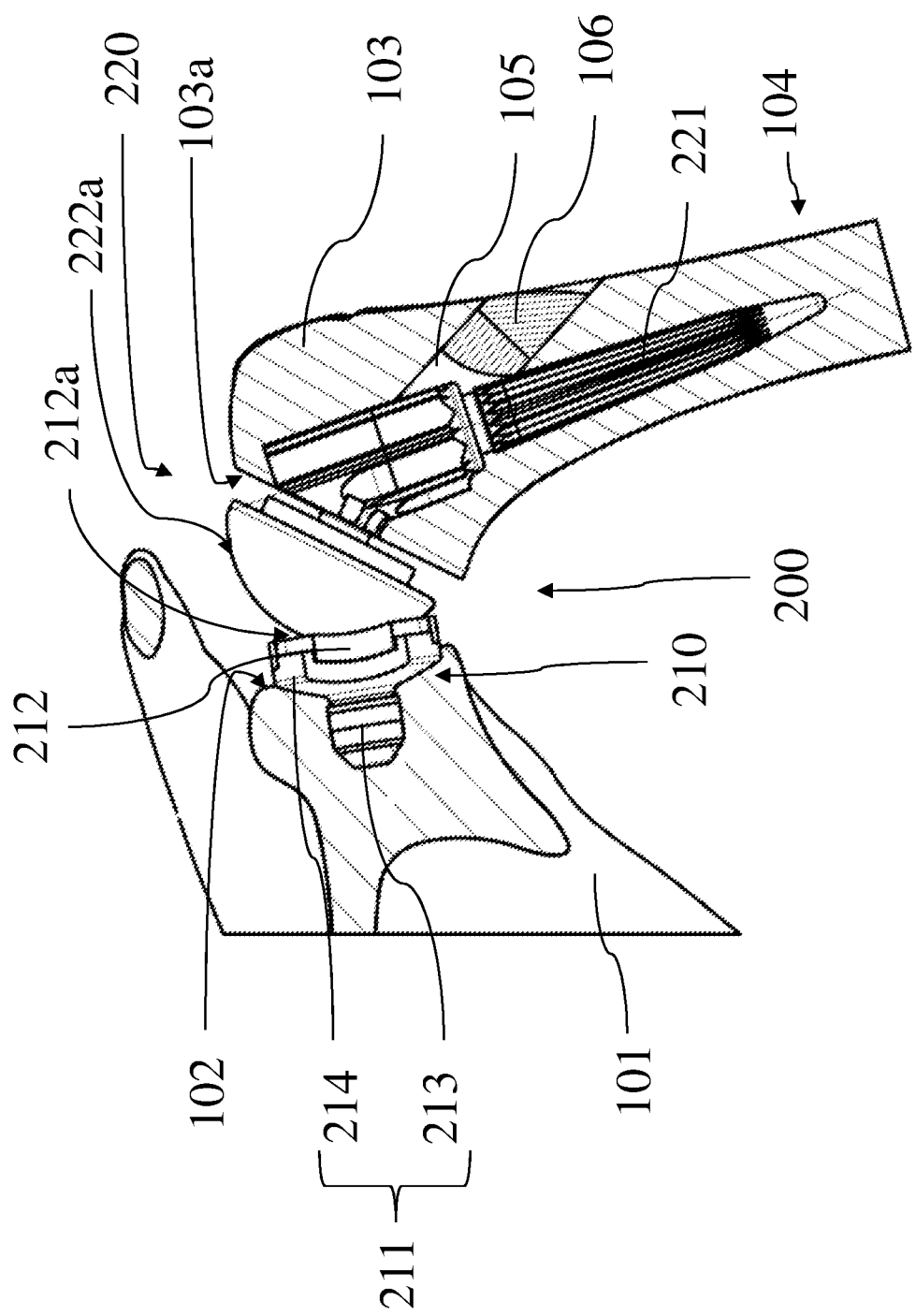
FIG. 18 shows diagrammatic partially sectioned view taken on a frontal plane of an exemplary anatomical total shoulder prosthesis with a glenoid component implanted in the shoulder joint of FIG. 1 by means of the method and the instruments according the present invention.

FIG. 18 shows in diagrammatic form an exemplary anatomical total shoulder prosthesis 200 with a glenoid component 210 implanted in the shoulder joint 100 of FIG. 1 by means of the method and the instruments according to the present invention.

The exemplary anatomical prostheses 200 shown in FIG. 18 comprises, on one side, a glenoid component 210 comprising a glenoid anchor 211 associated with the glenoid cavity 102 of the scapula 101 and a concave articular insert or bearing 212 fixed to the glenoid anchor 211, and, on the other side, a humeral component 220 integrated in the humerus 104 defining a convex articular surface cooperating with the concave bearing 212, recreating the shoulder joint.

The glenoid anchor 211 shown in FIG. 18 comprises two pieces fixed together by means an interference fit: a peg 213 and a baseplate 214.

The peg 213 is substantially in the form a pin which has an internally hollow conical sleeve defining a conical internal cavity 213a therethrough the peg 213. The conical internal cavity 213a extends from an open hole 213c at a tapered distal end 213b to an opposite proximal opening 213d. The open hole 213c is correspondingly threaded so as to be engaged by means of a rod threaded end, as will be described in detail later.

The baseplate 214 comprising a flange 214a having a concave surface wherein is fixed the bearing 212 opposite to a convex surface from which protrudes a conical lug 214b. A baseplate passage 214d longitudinally extends therethrough the baseplate 214 from the concave surface through the lug 214b. The function of the baseplate passage 214d will be described in detail later in the description.

A conical coupling with controlled mechanical interference between the lug 214b of the baseplate 214 and the internal cavity 213a of the peg 213 is envisaged. The flange 214a comprising two diametrically opposed through baseplate holes 214c to fasten the baseplate 214 to the glenoid cavity 102 by means of respective bone screws.

FIG. 18 shows the baseplate 214 fitted with the peg 213, the peg 213 inserted into a peg hole 107 made into the glenoid cavity 102 and the convex surface of the baseplate 214 attached to the glenoid cavity 102.

As is also shown in FIG. 18, the humeral head 103 has a humeral head top 103a resected and a cylindrical through trans-humeral hole 105 extending in medio-lateral direction. The function of the resection and of the trans-humeral hole will be clear later.

The humeral component 220 comprises a medullary stem 221 inserted inside the medullary cavity of the humerus 104. At the top end the stem 221 widens into a head 222 which has on its side opposite to the stem 221 a convex articular surface 222a with a semispherical form having a different radius respect to that of the concave surface 212a of the bearing 212. Between the radii of the surfaces 212a and 222a there is a predetermined mismatch. When the prosthesis 200 is implanted, as shown in FIG. 18, the surfaces 212a and 222a are directed in contact against each other, allowing the various movements required by the shoulder. Advantageously, according to the present invention, the surgical method and the instruments described here allow an implant of the glenoid component in a less invasive manner compared to the known surgical techniques, in particular the method does not consider the exposure of the glenoid cavity preserving the subscapularis muscle. The steps of the surgical method developed by the Applicant may be easily understood from the sequence shown in FIG. 2 onwards. The description which follows does not intend to describe all the steps involved in the surgical implant of an anatomical shoulder prosthesis, but only those steps which are most important and relevant to the description of the invention; therefore, detailed explanations such as to how the patient is positioned or how the humeral component is implanted into the humerus head of the humerus or the glenoid cavity are surgically exposed will be omitted.

For the purposes of the present invention, a delto-pectoral incision is provided into the skin and underneath tissues in order to provide a surgical access to the shoulder joint 100.

Once the surgical access is made, the humeral head 103 undergoes firstly a drilling operation to make the through trans-humeral hole 105.

Figure 3:
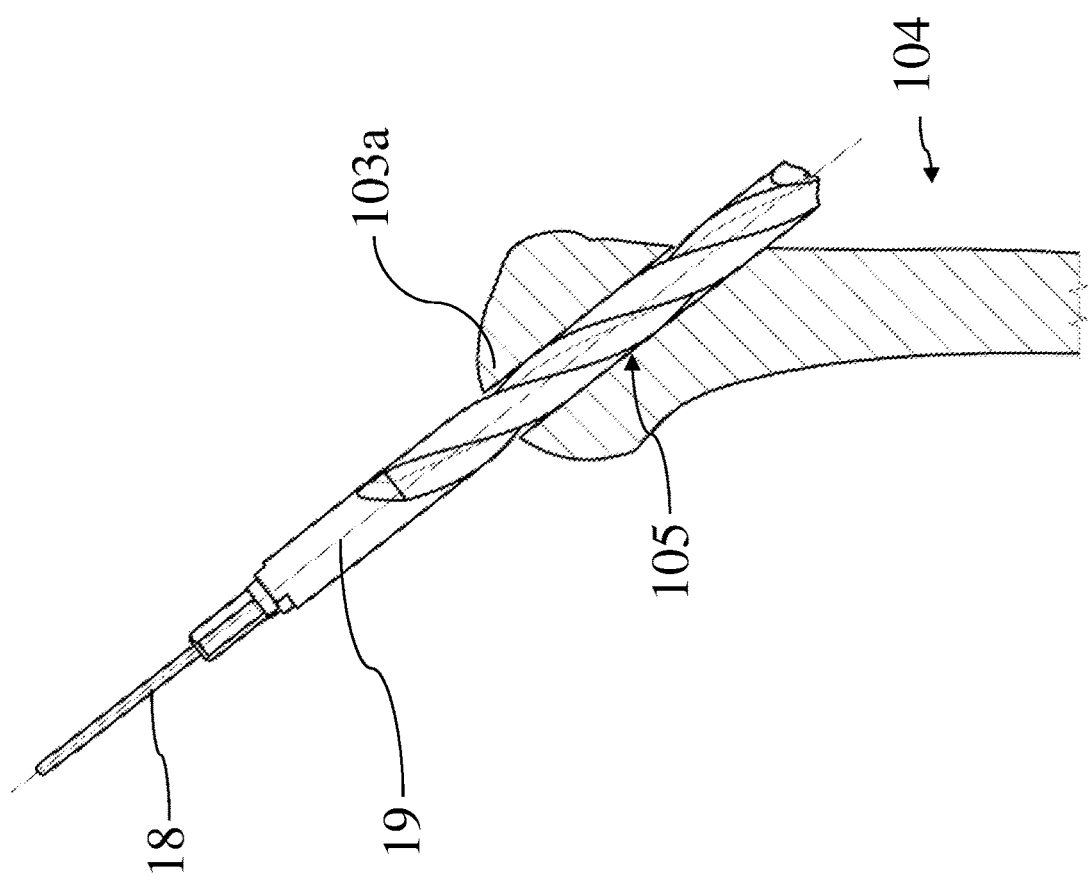
FIG. 3 is diagrammatic sectioned view taken on a frontal plane of the humeral head during the step of making a through trans-humeral hole into the humeral head by a cannulated drill bit guided by the guidewire of FIG. 2 according to the method of the present invention.

As shown in FIG. 3, the hole 105 is substantially cylindrical and extends in medio-lateral direction from the humeral head top 103a. As will be described below in detail, the hole 105 is advantageously used for the insertion of surgical instruments.

In order to perform the hole 105, the humeral head top 103a is exposed through the surgical access dislocating the humerus 104 by means of an abduction and an externally rotation of the patient arm.

Figure 2:
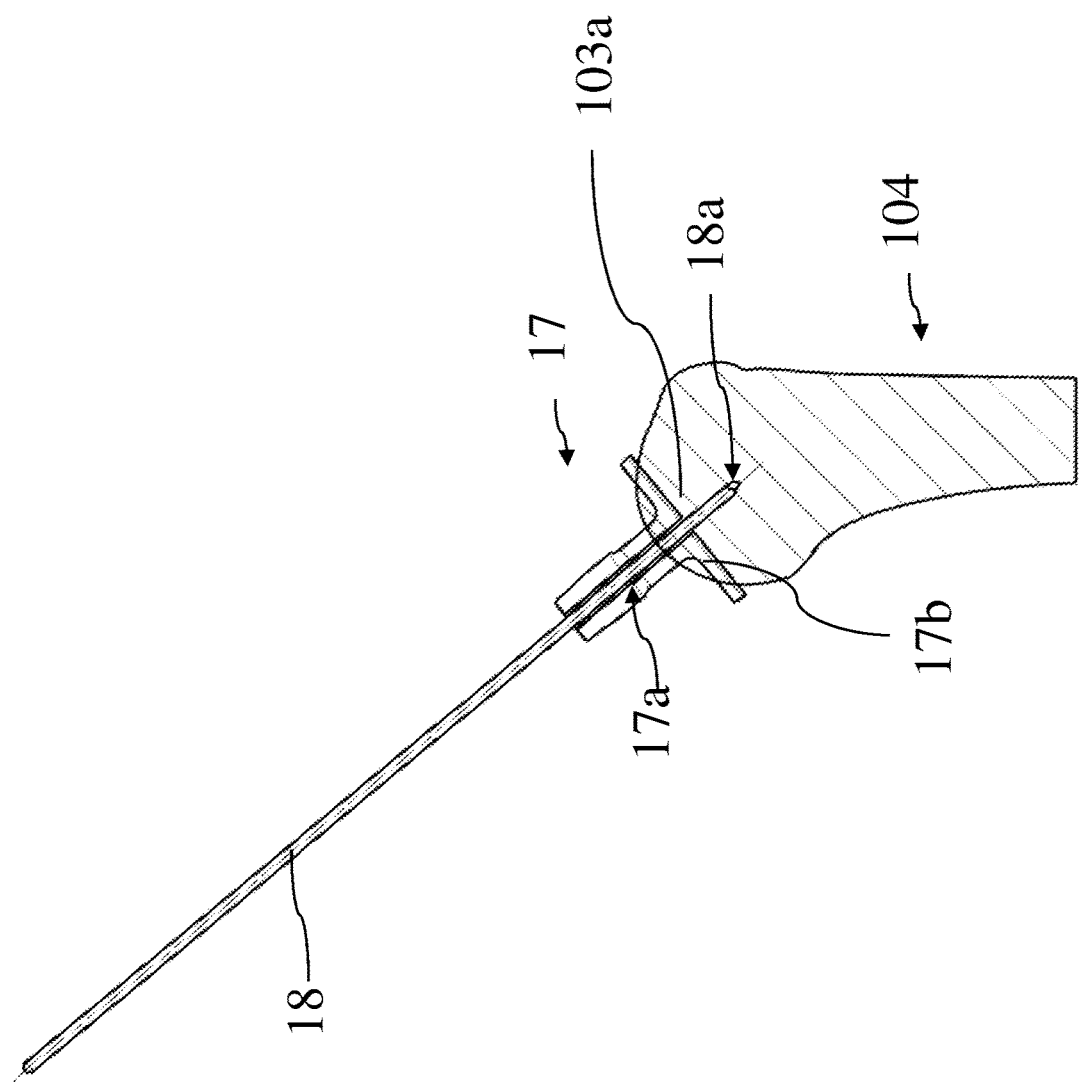
FIG. 2 is a diagrammatic sectioned view taken on a frontal plane of the humeral head during the insertion of a guidewire tip into the humeral head by means of a centering device according to the method of the present invention.

The through trans-humeral hole 105 could be made by a common cylindrical cannulated drill bit 19 guided by a guidewire 18. As shown in FIG. 2, a cannulated centering device 17 could be used to guide the insertion of the guidewire 18 substantially at the center of humeral head top 103a.

The exemplary cannulated centering device 17 shown in FIG. 2 comprising a cylindrical centering device guide passage 17a for the introduction of the guidewire 18 and an abutting portion 17b that abuts against the humeral head top 103a aligning the longitudinal axis of the centering device guide passage 17a with the center of humeral head top 103a in a medio-lateral direction.

Once the centering device 17 is located, a guidewire tip 18a of the guidewire 18 is introduced into the guide passage 17a until it is inserted into the humeral head 103. Then, the centering device 17 is extracted and the inserted guidewire 18 is used as a guide by the drill bit 19 for making the cylindrical through trans-humeral hole 105, as shown in FIG. 3. Making the hole 105 it is important to pay attention to not damage the tissues and the skin when the drill bit 19 escapes from the lateral side of the humerus 104.

As the hole 105 is made, the drill bit 19 and the guidewire 18 are extracted through the delto-pectoral incision.

Figure 17:
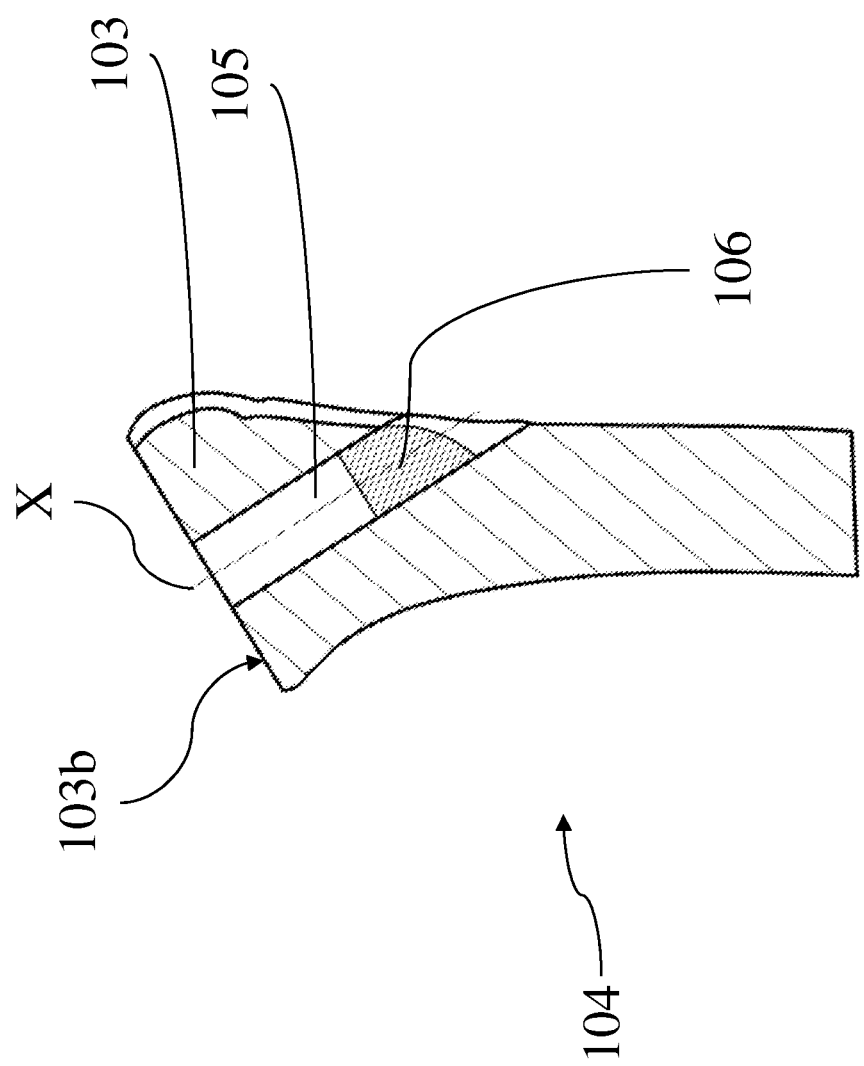
FIG. 17 shows a diagrammatic sectioned view taken on a frontal plane of the humeral head with a bone graft inserted into the trans-humeral hole according to the present invention.

The humeral head top 103a is preferably resected along a coronal direction substantially orthogonal to a through trans-humeral hole axes X, as shown in FIG. 17, defining a resection surface 103b lying on the coronal plane. The resected humeral head top could be used for extracting a cylindrical bone graft 106, having a diameter substantially equal to the internal diameter of the hole 105. The bone graft 106 could be advantageously inserted into the through trans-humeral hole 105 in order to at least partially restore the bone continuity reducing the probability of crack formation when the bone will be loaded.

Obviously, the person skilled in the art will understand that the bone graft 106 could be extract using a core drill.

Figure 19:
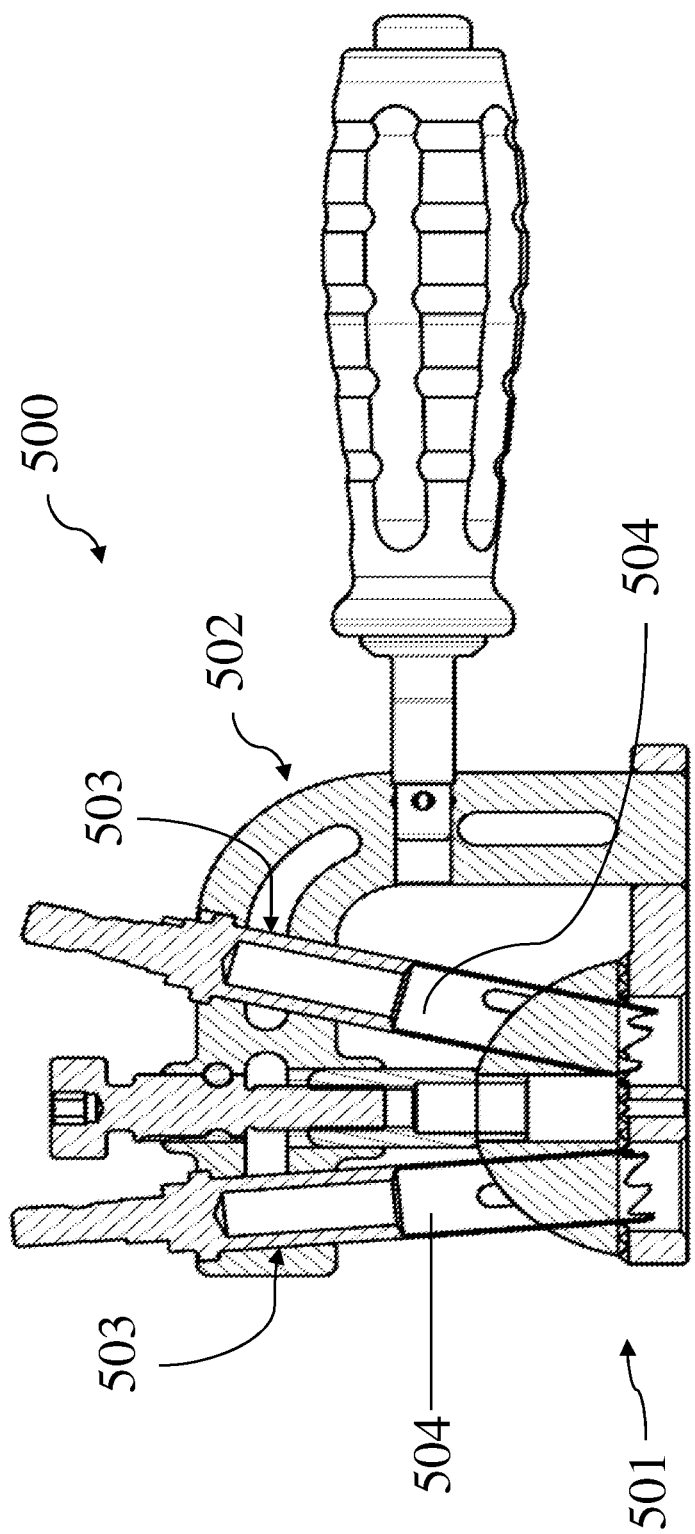
FIG. 19 shows a diagrammatic partially sectioned view of an exemplary core drill instrument that could be used to obtain the bone graft from the resected humeral head top according to the method of the present invention.

FIG. 19 shows an exemplary embodiment of a core drill instrument 500. The core drill instrument 500 shown in FIG. 19 comprises a vice 501 fixed to a vice body 502. Two core drill guide holes 503 are provided through the vice body 502. Said core drill guide holes 503 allows to guide the insertion of corresponding core drills 504 into the resected humeral head top positioned into the vice 501.

Once the through trans-humeral hole 105 is made, the patient arm is adducted and internally rotated in order to return the humeral head 103 in the original position facing the glenoid cavity 102.

The next step of the surgical method consists in separating the humeral head 103 from the glenoid cavity 102 defining a gap G between them.

To do that, it is advantageously provided a retractor instrument 10, through the delto-pectoral access, that allows to keep free the access to the through trans-humeral hole 105 and the glenoid cavity 102, while keeping a predetermined distance between the humeral head 103 and the glenoid cavity 102.

Figure 4:
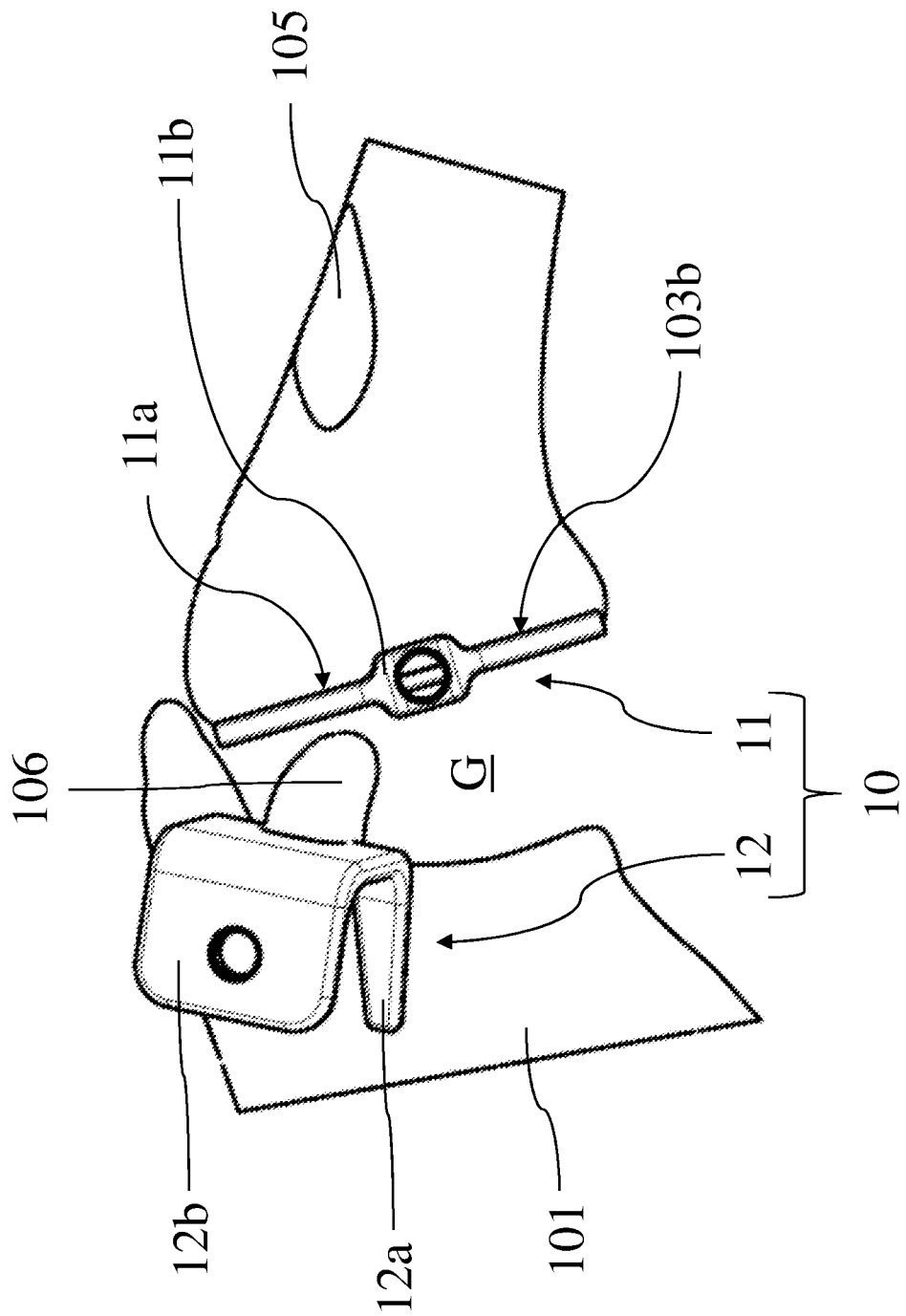
FIG. 4 shows a diagrammatic top view of a retractor instrument, implanted according to the present invention, keeping a predetermined glenohumeral clearance between the humeral head and the glenoid cavity.

FIG. 4 shows a top view of the retractor instrument 10 in operation abutting against the scapula 101 and the humeral head 103.

The exemplary retractor instrument 10 shown in FIG. 4 comprising a first abutting element 11 and a second abutting element 12.

The first abutting element 11 is shaped to abut against the humeral head 103 keeping free the access to the through trans-humeral hole 105.

In particular, the first abutting element 11 has a substantially ring shape with a plane abutting surface 11a directly abutting against the resection surface 103b of the humeral head 103. In this way, the first abutting element 11 surrounds the through trans-humeral hole 105 that is in communication with the gap G.

Figure 21:
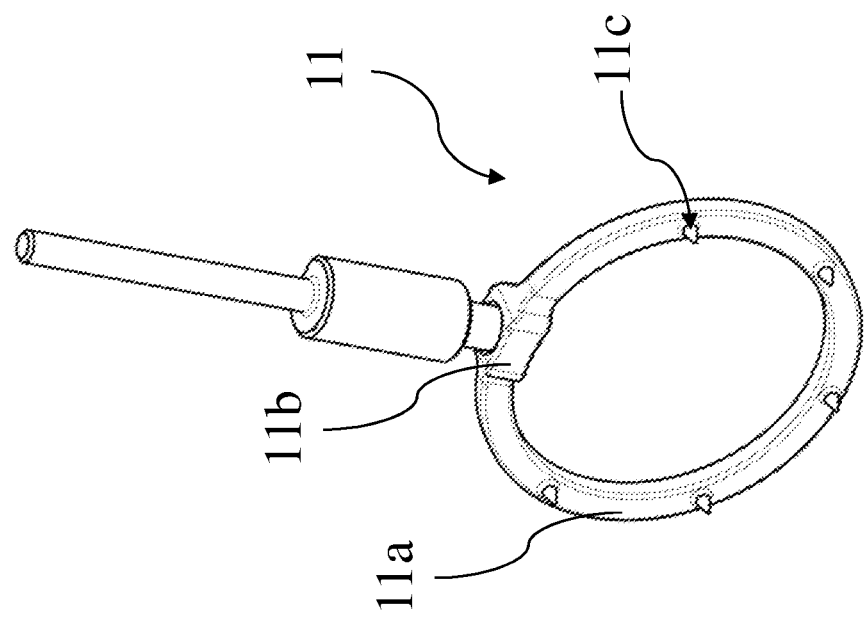
FIG. 21 shows a diagrammatic prospective view of a first abutting element of the retractor instrument of FIG. 4.

The abutting surface 11a is provided with anchoring means for promoting grip between the first abutting element 11 and the bone preventing relative movements when the abutting surface 11a abuts against the humeral head. In a favorite embodiment of the first abutting element 11 shown in FIG. 21, the anchoring means comprise a plurality of spikes 11c protruding from the abutting surface 11a. The spikes 11c are preferably uniformly distributed along the abutting surface 11a.

In alternative embodiments of the first abutting element 11, the anchoring means could comprise a rugosity of the abutting surface 11a and/or other features to improve the grip.

The second abutting element 12 is instead shaped to at least partially abut against the scapula 101.

In particular, the second abutting element 12 is shaped to abut against the coracoid process 106 leaving free the glenoid cavity 102.

Figure 22:
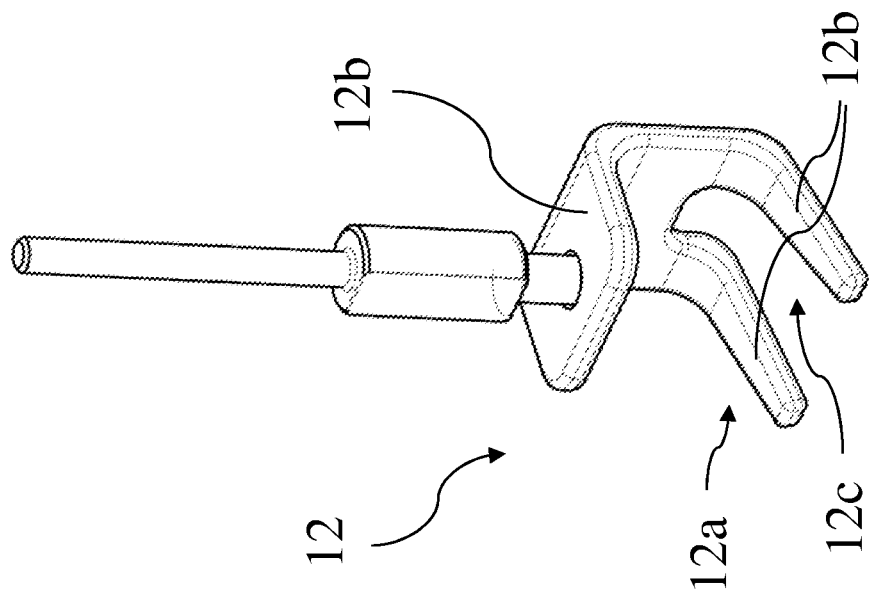
FIG. 22 shows a diagrammatic prospective view of a second abutting element of the retractor instrument of FIG. 4.

A favorite embodiment of the second abutting element 12, singularly shown in FIG. 22, comprises an abutting portion 12a having a substantially flat U-shape that inferiorly embraces the coracoid process 106. In particular, the abutting portion 12a is provided with two folded prongs 12b that define an abutting portion recess 12c. As shown in FIG. 4, the abutting portion recess 12c is inserted inferiorly around the coracoid process 106 until the bottom of the recess 12c abuts against the coracoid process 106.

In order to separate the humeral head 103 and the glenoid cavity 102, the first abutting element 11 is laterally moved and/or the second abutting element 12 is medially moved. To this purpose, the first and the second abutting elements 11, 12 comprises a first and a second coupling portion 11b, 12b, respectively, to be coupled to a divarication tool.

Figure 23:
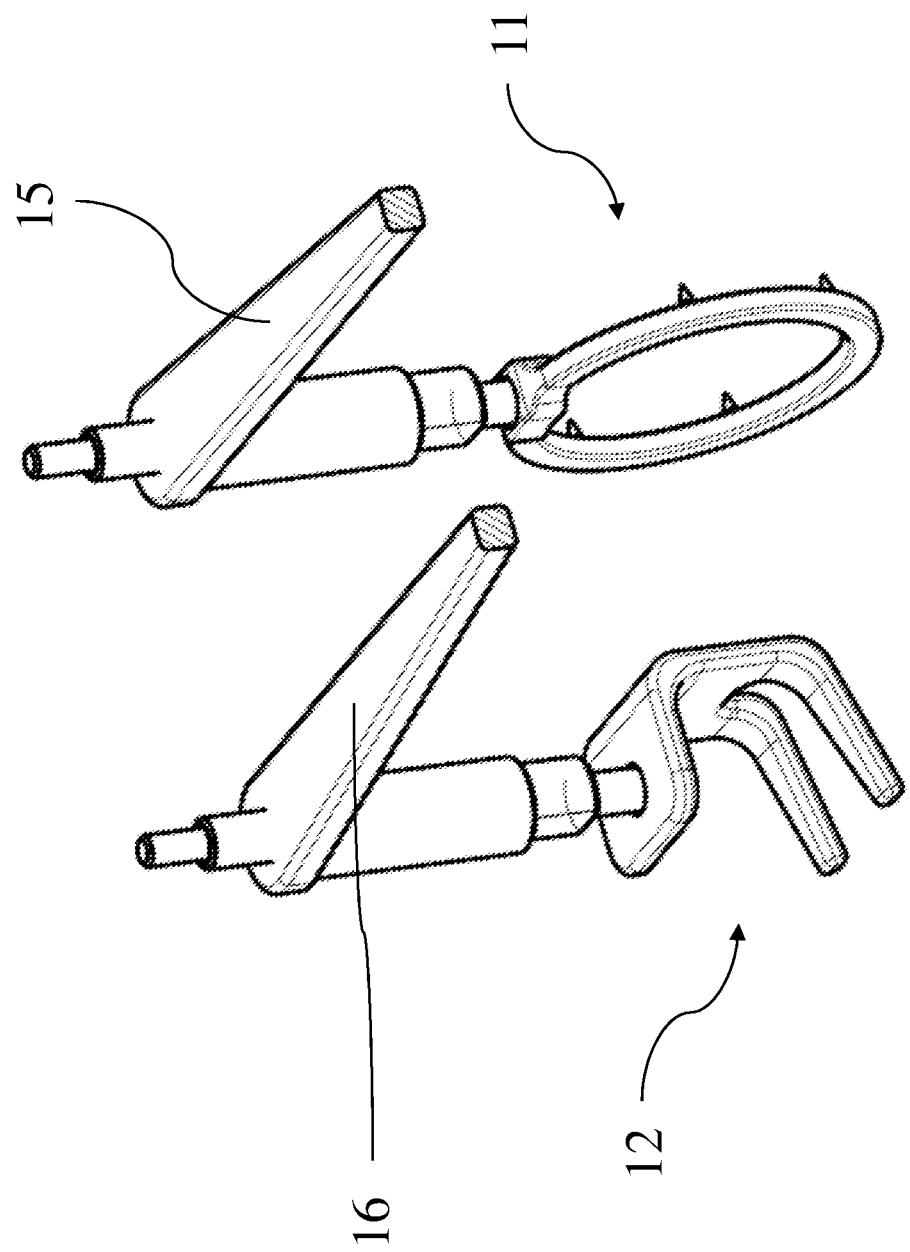
FIG. 23 shows a diagrammatic prospective view of the first and the second abutting element of the retractor instrument of FIG. 4 respectively coupled to a first and a second arm of a surgery clamp.

Obviously, the person skilled in the art will understand that, the divarication tool could be a common surgery clamp. In this case, the first and the second coupling portion 11b, 12b could be fixed to a free end of a first and a second clamp arm 15, 16, respectively. FIG. 23 shows the first and the second abutting elements 11, 12 coupled to exemplary first and second clamp arm 15, 16.

Preferably, the clamp is provided with blocking means for fixing the distance between the first and the second abutting elements 11, 12, and so the width of the gap G between the humeral head 103 and the glenoid cavity 102.

In alternative embodiments of the retractor instrument 10, the first and the second abutting elements 11, 12 could be of different shapes. For example, the first abutting element 11 could have a C-shape or other shapes partially surrounding the trans-humeral hole 105. The second abutting element 12 could abut against the acromion or at least partially around the glenoid cavity 102.

In other embodiments the second abutting element 12 could also have anchoring means.

Although the retractor instrument 10 is kept in place for all the rest of the surgery method, it is not shown in FIG. 5 onwards that show the next steps of the method as will be described below.

When the retractor instrument 10 is placed and the gap G between the glenoid cavity 102 and humeral head 103 is kept, a trans-deltoid incision into the skin and underneath tissues is made laterally to the humeral head 103 in order to provide a trans-deltoid access to the through trans-humeral hole 105.

Once the trans-deltoid access is provided, it is inserted therethrough a cannulated guide retractor 20 for guiding the insertion of surgery instruments into the gap G through the trans-deltoid incision and the trans-humeral hole 105, as will be described in detail later.

Figure 5:
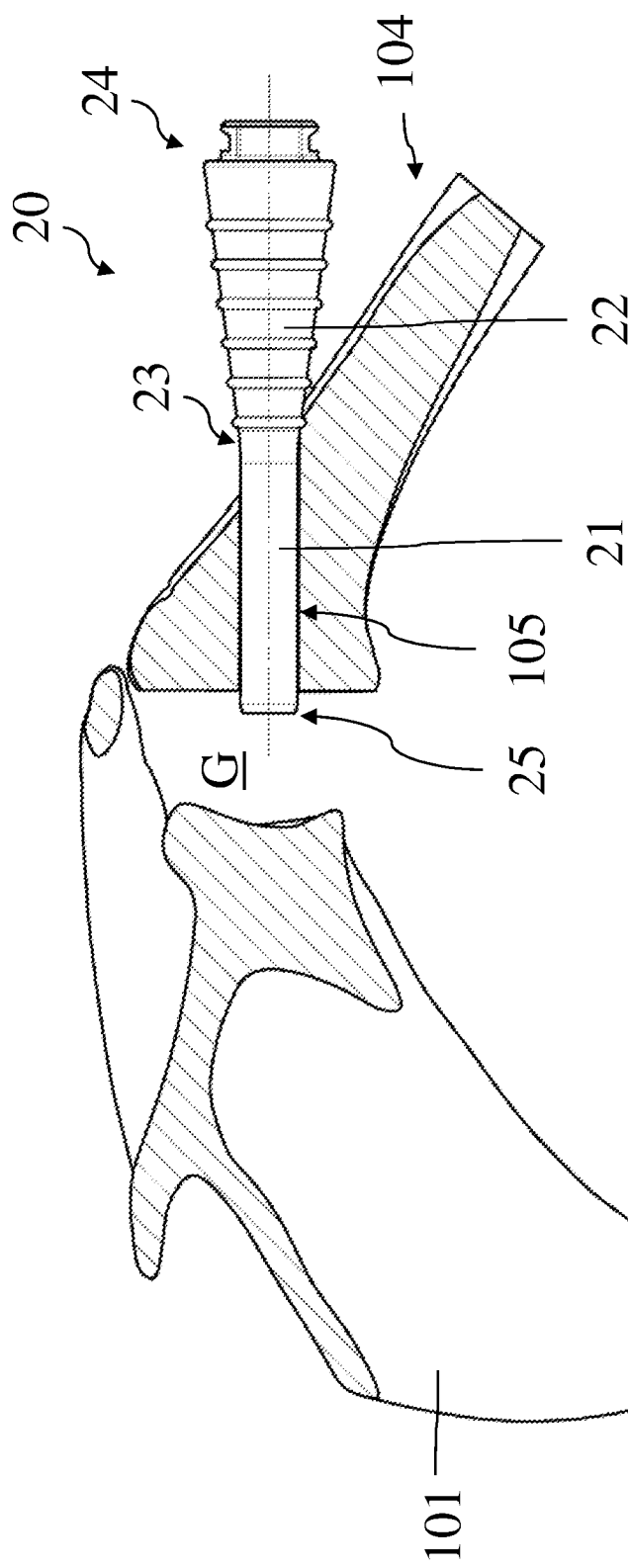
FIG. 5 shows a diagrammatic sectioned view taken on a frontal plane of the shoulder of FIG. 1 with a retractor instrument implanted (not shown) and a cannulated guide retractor inserted into the through trans-humeral hole according to the present invention.

An exemplary cannulated guide retractor 20 is shown in FIG. 5. Said cannulated guide retractor 20 having a substantially tube shape. A cannulated guide retractor passage extends therethrough along all the cannulated guide retractor 20 from a first cannulated guide retractor opening 24 at the trans-deltoid incision to a second cannulated guide retractor opening 25 at the gap G.

The cannulated guide retractor 20 further comprising two adjacent portions having two different specific functions: an insertion portion 21 and a retracting portion 22. The cannulated guide retractor passage extends therethrough along both the insertion portion 21 and the retracting portion 22.

As can be seen from FIG. 5, the inserting portion 21 has a cylindrical shape with outer diameter slightly less than the inner diameter of the through trans-humeral hole 105 wherein it is concentrically inserted. The second cannulated guide retractor opening 25 falls into the gap G and an inserting portion extremity 23, adjacent to the retracting portion 22, is laterally outside of the humeral head 103.

The retracting portion 22 has instead a substantially conical shape with an outer diameter that increases along the retracting portion 22 from the insertion portion extremity 23 to the first cannulated guide retractor opening 24. The retracting portion 22 further comprising longitudinally separated annular ribs 26 on an external surface.

As shown in FIG. 5, the insertion portion 21 is inserted into the through trans-humeral hole 105 in such a way that it could stabilize the cannulated guide retractor 20 and ensure an instrument inserted through the trans-deltoid incision to reach the gap G. The retracting portion 22 stays outside of the hole 105 and, thanks to its tapered shape, advantageously keeps the soft tissues between the trans-deltoid incision and the humeral head 103 retracted. The annular ribs 26 facilitates keeping soft tissues retracted increasing the grip between the device and the tissues.

Although the cannulated guide retractor 20 is kept in place for all the rest of the surgery method, it is not shown in FIG. 6 onwards showing the next steps of the method that will be described below.

Once the cannulate retractor 20 is placed, the glenoid cavity 102 is machined in order to shape the bone to accommodate the glenoid anchor 211.

The first machining step consists in milling of glenoid cavity 102 to remove the cartilage and expose the subchondral bone.

Figure 6:
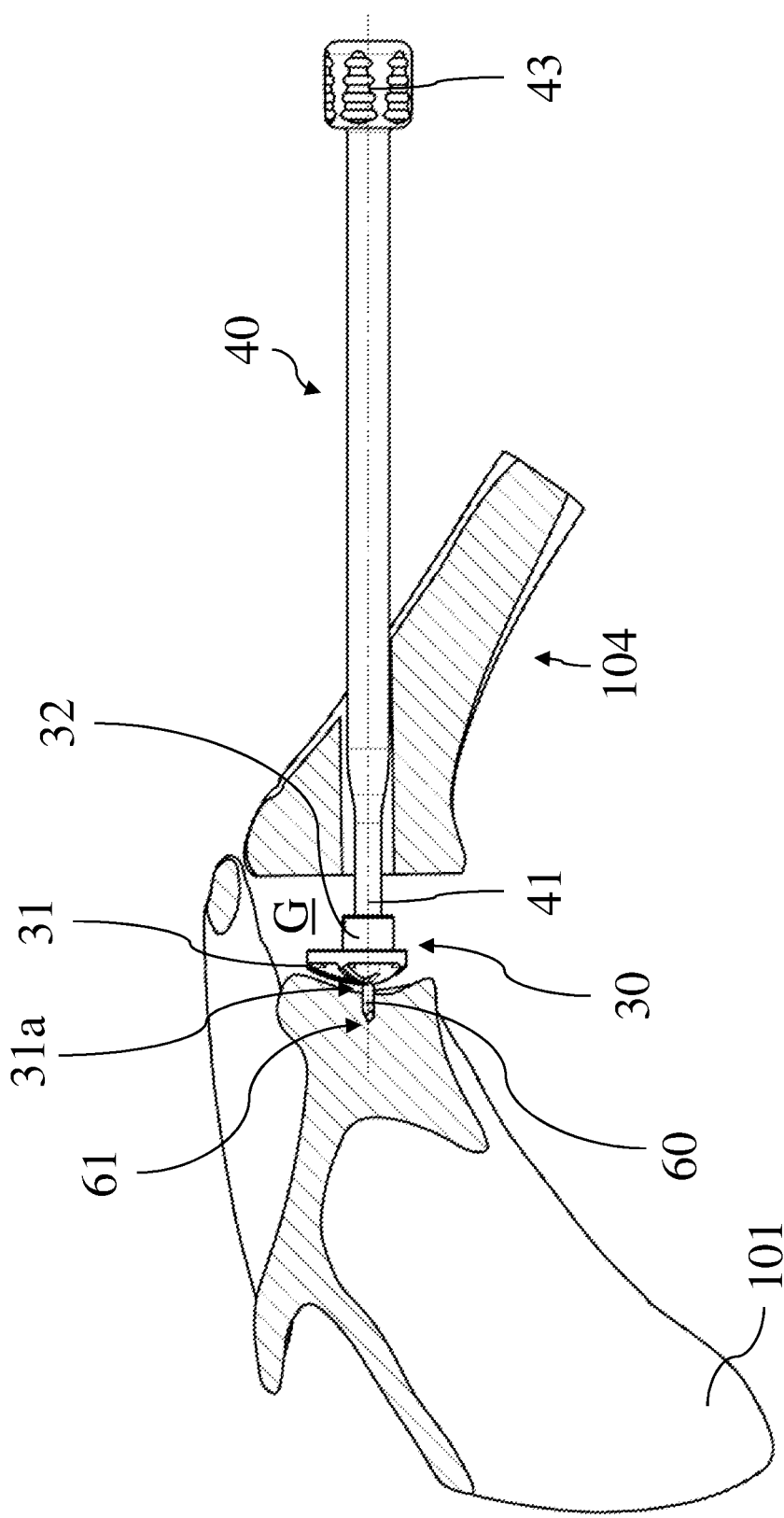
FIG. 6 shows a diagrammatic sectioned view of FIG. 5 with the retractor instrument and the cannulated guide retractor not shown, a cannulated guidewire guide inserted through the trans-humeral hole, the guidewire inserted into the glenoid cavity through the cannulated guidewire guide and a cannulated milling tool located on the glenoid cavity according to the present invention.
Figure 7:
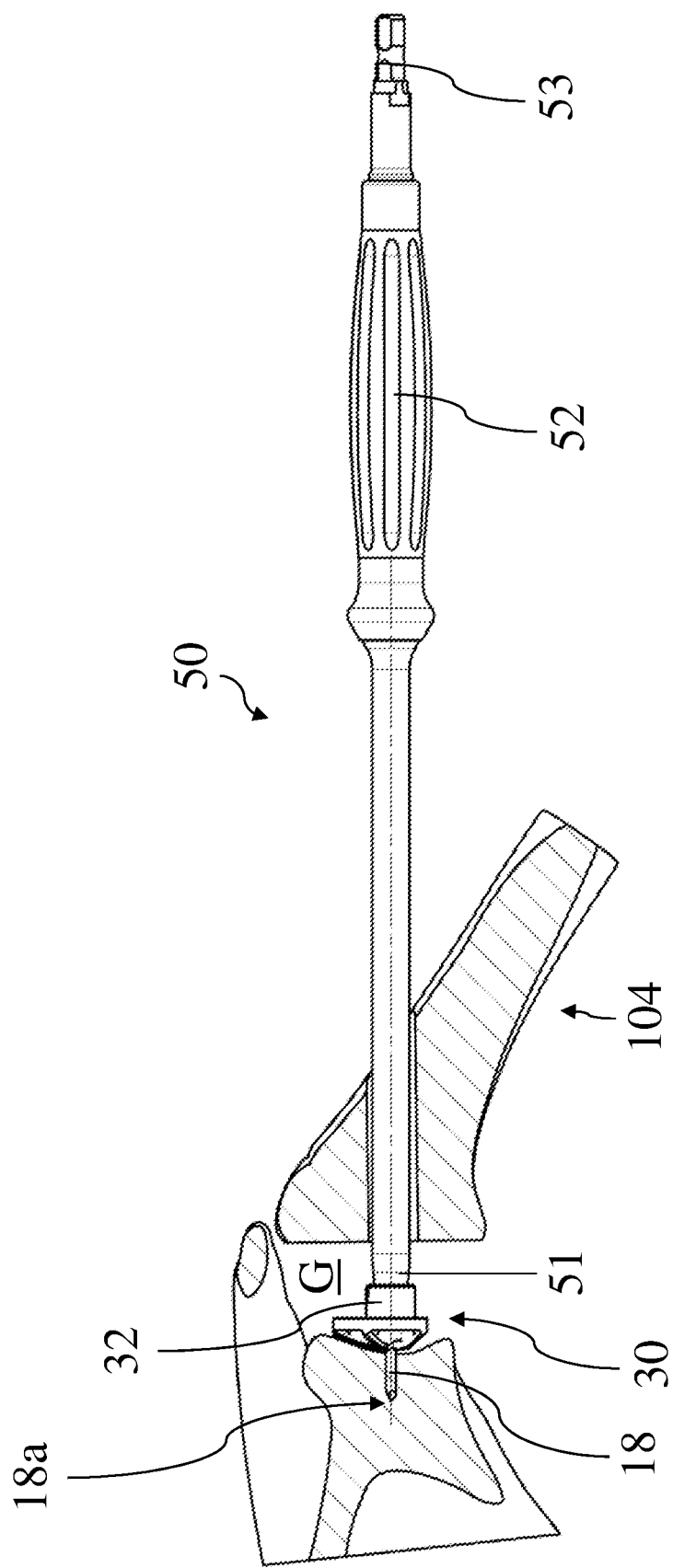
FIG. 7 shows a diagrammatic sectioned view of FIG. 5 with the retractor instrument and the cannulated guide retractor not shown, the guidewire inserted into the glenoid cavity through a cannulated milling tool located on the glenoid cavity, and a machining instrument stem coupled to the cannulated milling tool for milling the glenoid cavity according to the present invention.
Figure 8:
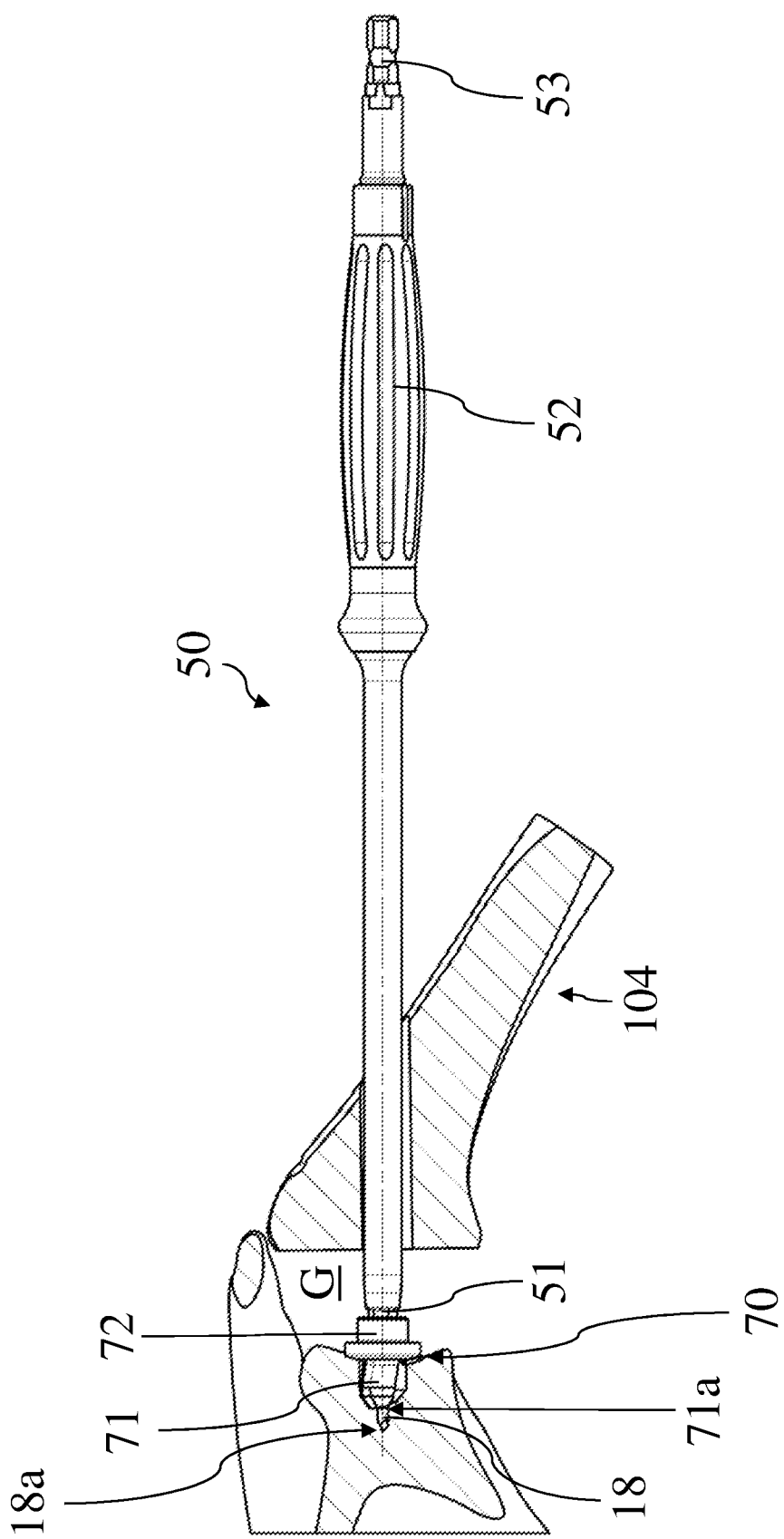
FIG. 8 shows a diagrammatic sectioned view of FIG. 5 with the retractor instrument and the cannulated guide retractor not shown, the guidewire inserted into the glenoid cavity through a cannulated reamer located on the glenoid cavity, and a machining instrument stem coupled to the cannulated reamer for making a hole for a peg of a glenoid anchor into the glenoid cavity according to the present invention.

As shown in FIGS. 6 and 7, a cannulated milling tool 30 is placed on the glenoid cavity 102 through the deltopectoral access.

Figure 29:
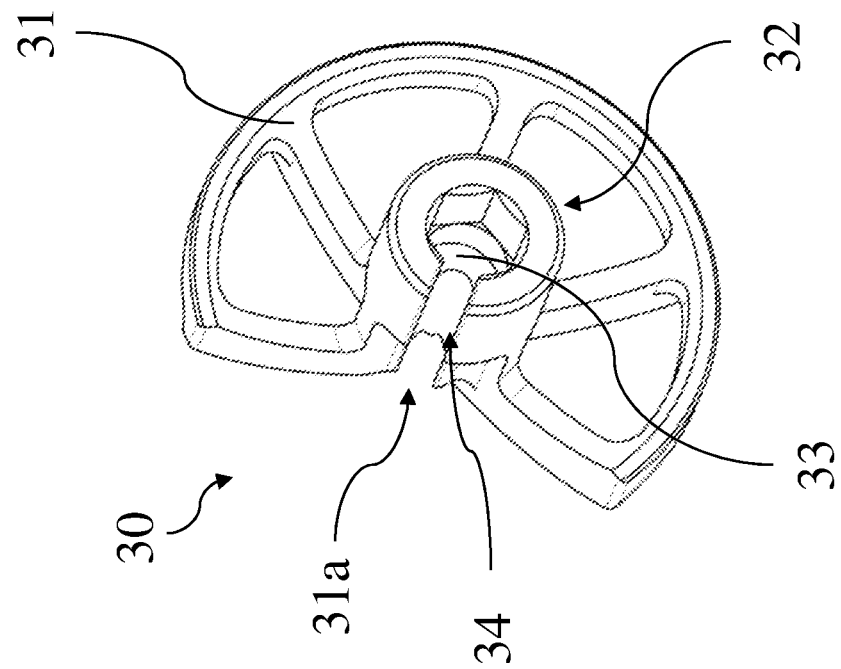
FIG. 29 shows a diagrammatic prospective view of a favorite embodiment of the cannulated milling tool of FIGS. 6 and 7 having a female coupling portion with a hexagonal section suitable to be coupled with the male machining instrument stem free end of the machining instrument stem of FIG. 24A.

A favorite embodiment of the cannulated milling tool 30, singularly shown in FIG. 29, comprises a cutting portion 31 having a substantially pierced semispherical shape with a cutting surface abutting against the glenoid cavity 102; at the apex of the cutting surface there is a cutting portion tip 31a. The cannulated milling tool 30 further comprising a milling tool coupling portion 32 consisting in a seat for inserting a cannulated guidewire guide coupling end 41 of a cannulated guidewire guide 40 and a machining instrument stem free end 51 of a machining instrument stem 50. As shown in FIG. 29, the seat of the coupling portion 32 has a hexagonal section.

A milling tool passage 33 longitudinally extends along the cannulated milling tool 30 from the tip 31a through the cutting portion 31, the coupling portion 32, into the seat.

The cannulated milling tool 30 further comprises a radial recess 34 that transversally extends from a longitudinal side of the cannulated milling tool 30 to the milling tool passage 33, The radial recess 34 having a width that is slightly bigger than the diameter of the guidewire 18.

Figure 26:
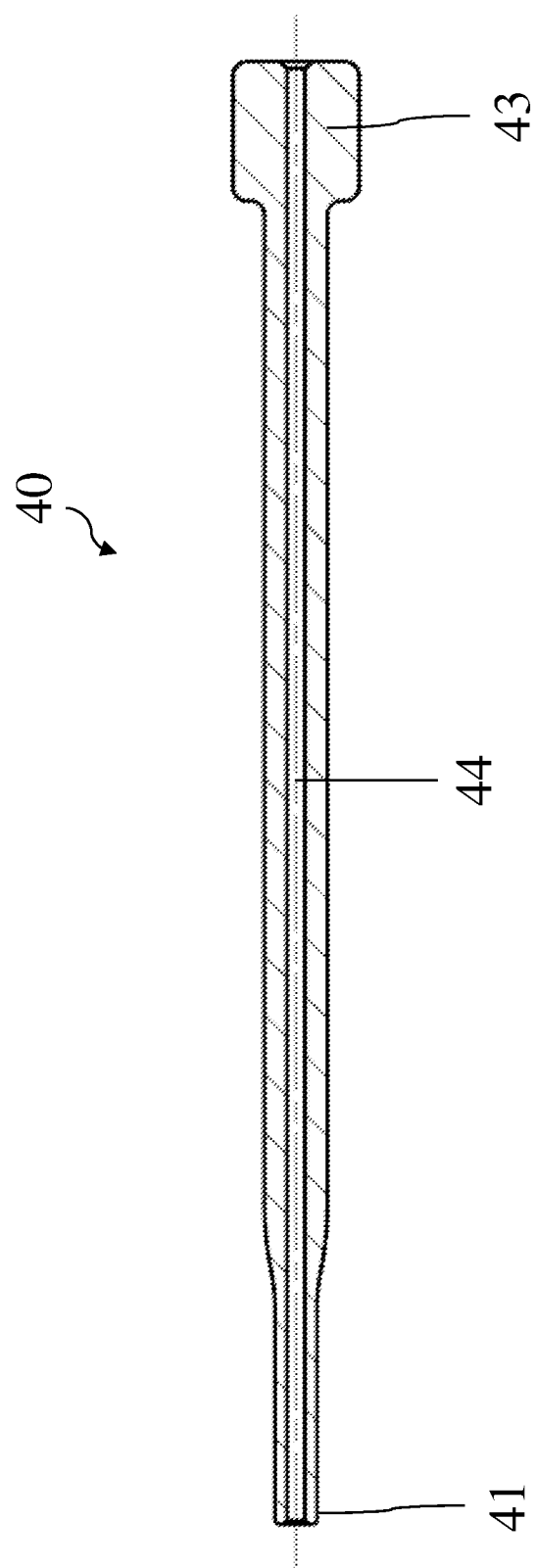
FIG. 26 shows a diagrammatic longitudinal sectioned view of the cannulated guidewire guide of FIG. 6.

As shown in FIGS. 6 and 26, the cannulated guidewire guide 40 as a substantially tubular shape with a cannulated guidewire guide passage 44 therethrough that connected the cannulated guidewire guide coupling end 41 and an opposite cannulated guidewire guide inlet end 43. The cannulated guidewire guide coupling end 41 preferably has a cylindrical section to be coupled with the hexagonal seat of the coupling portion 32 of the milling tool 30.

In an alternative embodiment a form fitting that allows to block the relative rotations between the cannulated guidewire guide 40 and the cannulated milling tool 30 may be provided.

The cannulated guidewire guide coupling end 41 is introduced through the trans-deltoid incision, the cannulated guide retractor passage and the gap G, and coupled in situ with the coupling portion 32, leaving the cannulated guidewire guide inlet end 43 outside of the patient body, as shown in FIG. 6.

Then, the guidewire tip 18a of the guidewire 18 is inserted through the cannulated guidewire guide inlet end 43, the cannulated guidewire guide passage, the milling tool passage 33, into the glenoid cavity 102, as also shown in FIG. 6. The guidewire 18 is preferably inserted into the glenoid cavity 102 orthogonal the neck of the glenoid compensating possibly eroded areas of the glenoid cavity surface.

The guidewire 18 is preferably the guidewire used for drilling the humeral hole 105, but it could be also another guidewire.

Obviously, the person skilled in the art will understand that the cannulated milling tool 30 acts as a centering device for inserting the guidewire 18 in a correct position and direction into the glenoid cavity 102.

According to FIG. 6, the guidewire 18 is inserted concentrically to the trans-humeral hole 105 along the axis X into the center of the glenoid cavity 102.

Once the guidewire 18 is inserted, the cannulated guidewire guide 40 and the cannulated milling tool 30 are decoupled. The cannulated guidewire guide 40 is extracted leaving the cannulated milling tool 30 and the guidewire 18 in place.

As shown in FIG. 7, a machining instrument stem free end 51 of a machining instrument stem 50 is inserted through the trans-deltoid incision, the cannulated guide retractor passage and the gap G, sliding along stem guidewire 18 and coupled with the coupling portion 32 of the milling tool 30

Figure 24A:
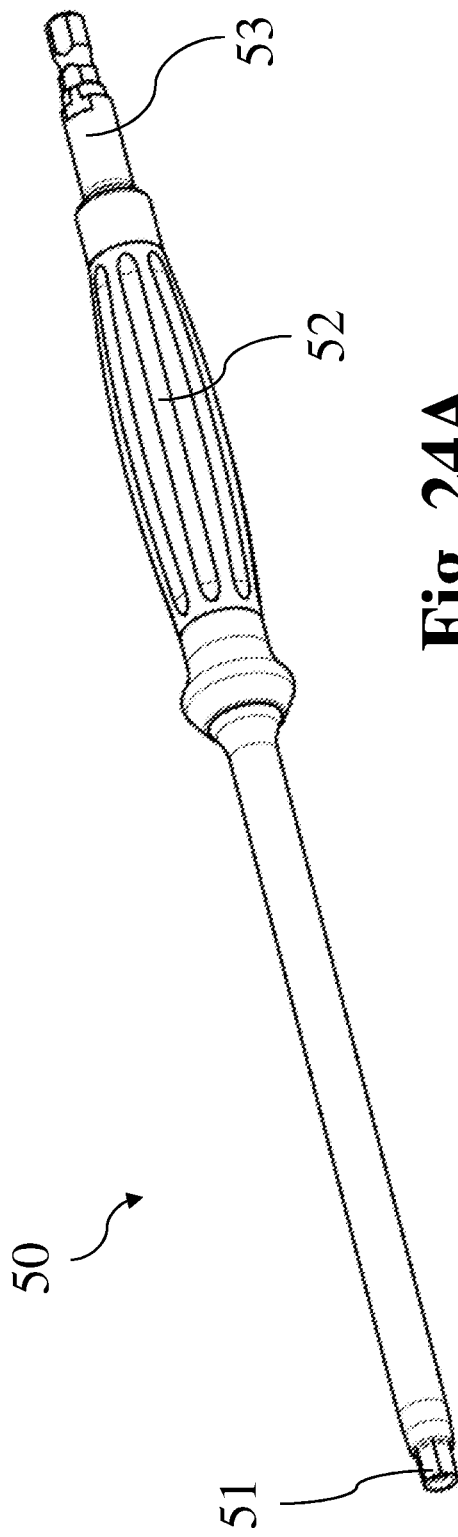
FIG. 24A shows a diagrammatic prospective view of a favorite embodiment of the machining instrument stem of FIGS. 7 and 8 having a male machining instrument stem free end with hexagonal section.
Figure 24B:
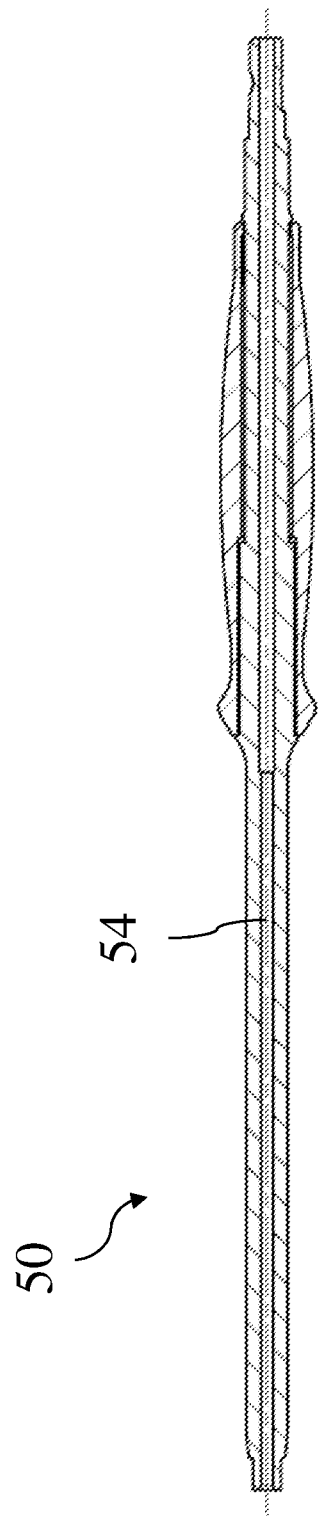
FIG. 24B shows a diagrammatic longitudinal sectioned view of the machining instrument stem of FIG. 24A.

FIGS. 24A and 24B show a favorite embodiment of the machining instrument stem 50. It is noted that the machining instrument stem free end 51 has a hexagonal section to be coupled with the hexagonal seat of the coupling portion 32 of the milling tool 30. In this way it is provided a form fitting that allows to block the relative rotations between the machining instrument stem 50 and the cannulated milling tool 30.

The machining instrument stem 50 also has a machining instrument stem passage 54. The insertion of the machining instrument stem 50 is guided by the guidewire 18 inserted into machining instrument stem passage 54.

The person skilled in the art will understand that the milling of the glenoid cavity 102 is performed rotating the milling tool 30 by means of rotating the machining instrument stem 50 manually using a handle 52 or mechanically connecting a motor coupling 53 with a motor of a milling machine.

When the milling is terminated, the machining instrument stem 50 and the cannulated milling tool 30 are separated. The cannulated milling tool 30 is transversally extracted from the guidewire 18 through the delto-pectoral incision leaving the guidewire 18 in place.

It should be clear to the reader that the easily extraction of the milling tool 30 is achieved thanks to the radial recess 34. Indeed, the radial recess 34 allows to extract the milling tool 30 leaving the guidewire 18 in place.

It is now described the following machining step of the surgery method that consists in reaming the glenoid cavity 102 in order to make the peg hole 107 for the fixation of the peg 213 of the glenoid anchor 211.

First of all, a cannulated reamer 70 is inserted through the delto-pectoral incision into the gap G.

Figure 30:
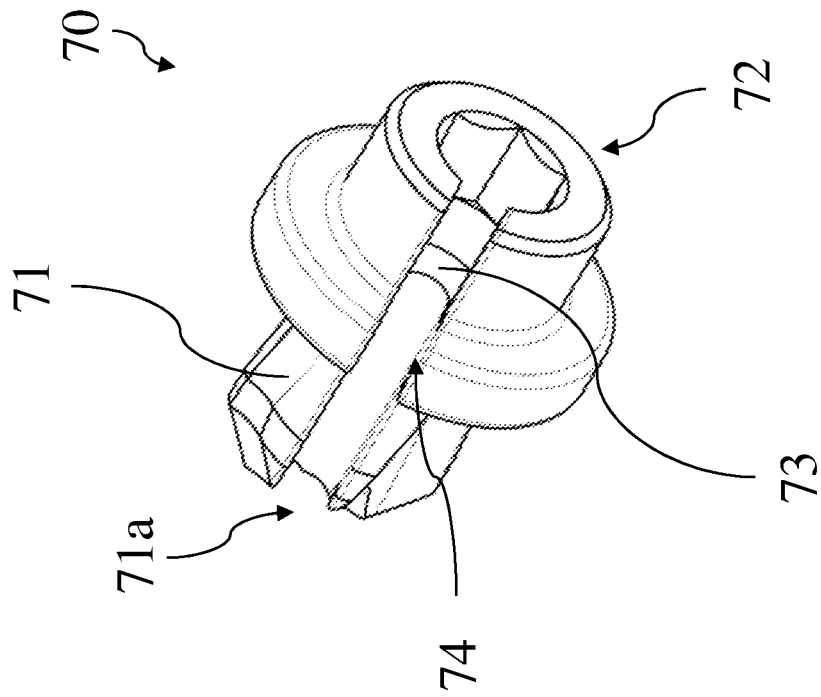
FIG. 30 shows a diagrammatic prospective view of a favorite embodiment of the cannulated reamer of FIG. 8 having a female coupling portion with a hexagonal section suitable to be coupled with the male machining instrument stem free end of the machining instrument stem of FIG. 24A.

A favorite embodiment of the cannulated reamer 70, singularly shown in FIG. 30, comprises a substantially conical cutting portion 71 with a reamer cutting portion tip 71a and a reamer coupling portion 72 consisting in a seat for inserting the machining instrument stem free end 51. A reamer passage 73 longitudinally extends along the cannulated reamer 70 from the tip 71a through the reamer cutting portion 71 and the reamer coupling portion 72. Likely the cannulated milling tool 30, the reamer coupling portion 72 has a seat with a hexagonal section for coupling the machining instrument stem free end 51.

The cannulated reamer 70 further comprises a reamer radial recess 74 that transversally extends from a longitudinal side of the cannulated reamer 70 to the cannulated reamer passage 73, The reamer radial recess 74 having a width that is slightly bigger than the diameter of the guidewire 18.

Once the cannulated reamer 70 is in the gap G, it is inserted in the guidewire 18 through the reamer radial recess transversally moving the cannulated reamer 70 in relation to the guidewire 18 until the reamer passage 73 embraces the guidewire 18.

It should be clear to the reader that the easily insertion of the guidewire 18 into the reamer passage 73 is achieved thanks to the reamer radial recess 74. Indeed, the reamer radial recess 74 allows to insert the cannulated reamer 70 with the guidewire 18 inserted into the glenoid cavity 102.

The machining instrument stem free end 51 is coupled with the reamer coupling portion 72. Then the peg hole 107 is made rotating the reamer 70 by means of the rotation of the machining instrument stem 50 manually using the handle 52 or mechanically connecting the motor coupling 53 with a motor of a milling machine.

When the peg hole 107 is made, the machining instrument stem 50 and the reamer 70 are separated, the machining instrument stem 50 and the guidewire 18 are extracted through the trans-deltoid incision, and the cannulated reamer 70 is extracted through the delto-pectoral incision.

The person skilled in the art will understand that the positive fitting provided between the female seat of the milling tool 30 or the reamer 70 and the male cannulated guidewire guide coupling end 41 and/or the male machining instrument stem free end 51 could be achieved with other section shapes.

Figure 25:
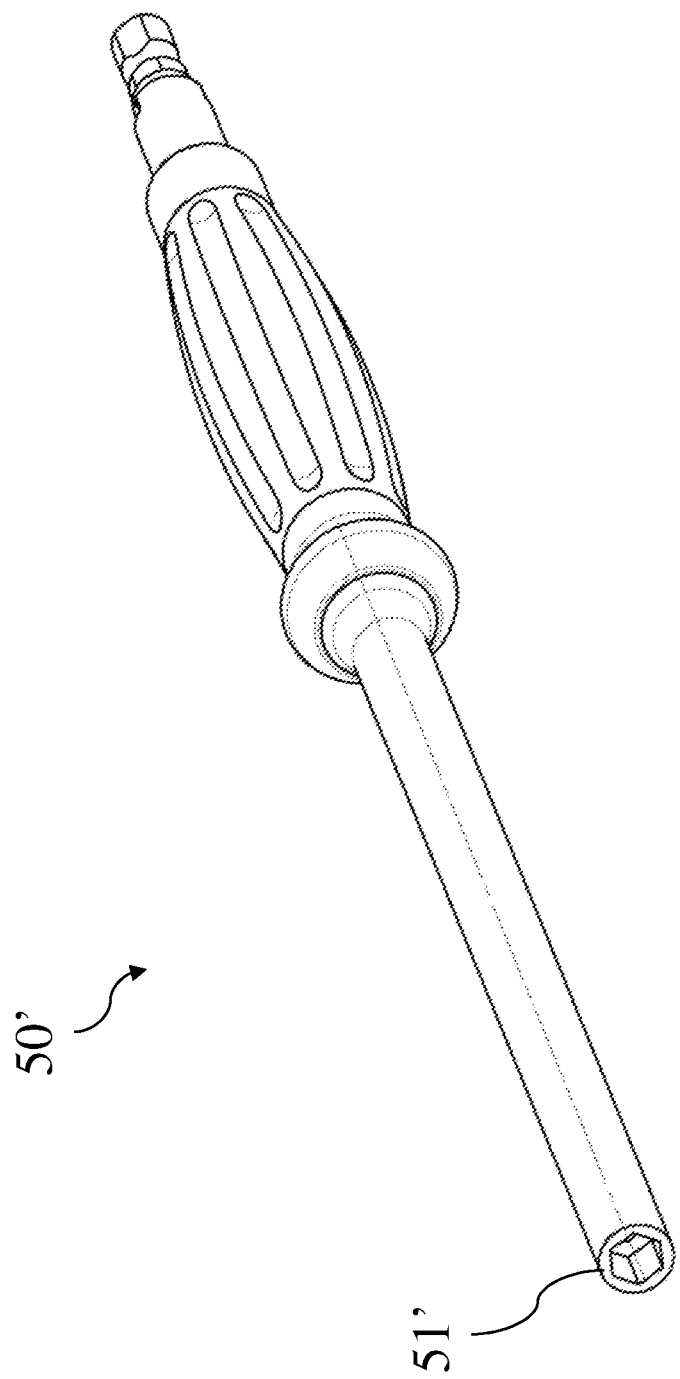
FIG. 25 shows a diagrammatic prospective view of an alternative embodiment of the machining instrument stem having a female machining instrument stem free end with hexagonal section.
Figure 32:
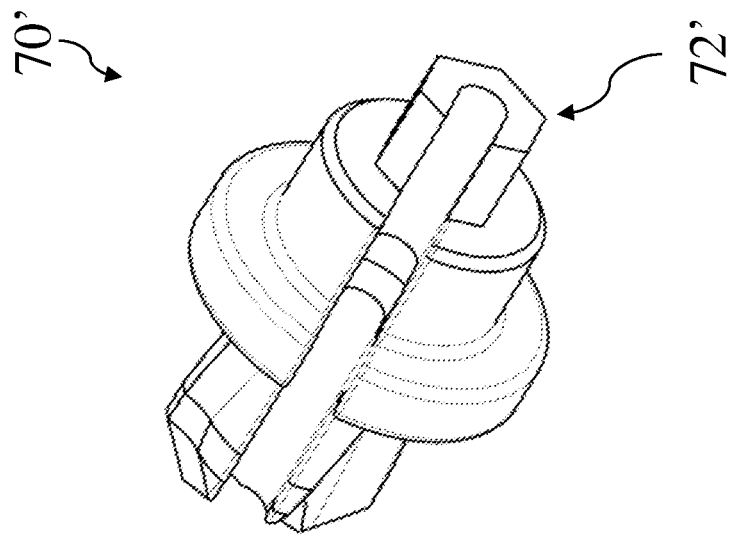
FIG. 32 shows a diagrammatic prospective view of an alternative embodiment of the cannulated reamer having a male coupling portion with a hexagonal section suitable to be coupled with the female machining instrument stem free end of the machining instrument stem of FIG. 25.
Figure 31:
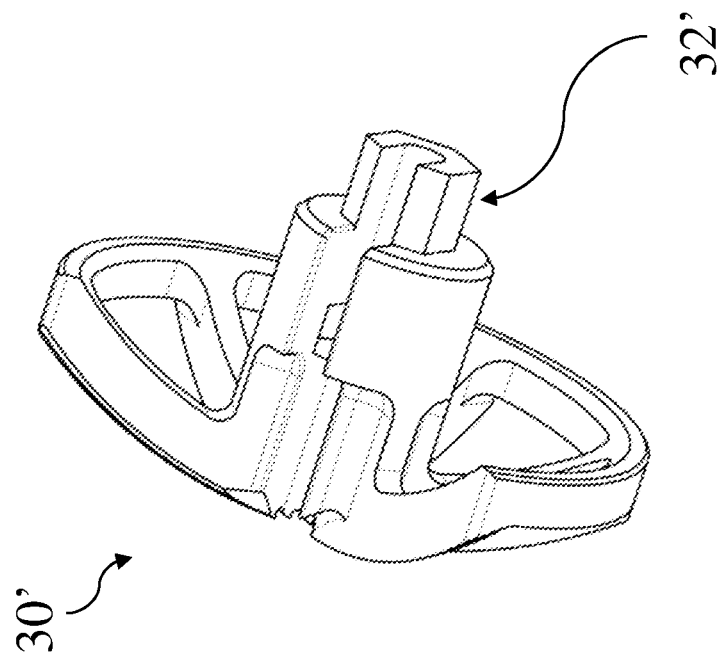
FIG. 31 shows a diagrammatic prospective view of an alternative embodiment of the cannulated milling tool having a male coupling portion with a hexagonal section suitable to be coupled with the female machining instrument stem free end of the machining instrument stem of FIG. 25.

In an alternative embodiment, the female seat could be provided at the cannulated guidewire guide coupling end and/or the machining instrument stem free end 51' of the machining instrument stem 50', as exemplary shown in FIG. 25; and the male element could be provided at the coupling portions 32' and 72' of the cannulated milling tool 30' and the cannulated reamer 70', as exemplary shown in FIGS. 31 and 32. At this stage, the glenoid cavity 102 has been shaped to accommodate the glenoid anchor 211, and so the glenoid anchor 211 is fixed according to the surgery method steps illustrate in FIGS. 9-16, that will be described below.

Figure 9:
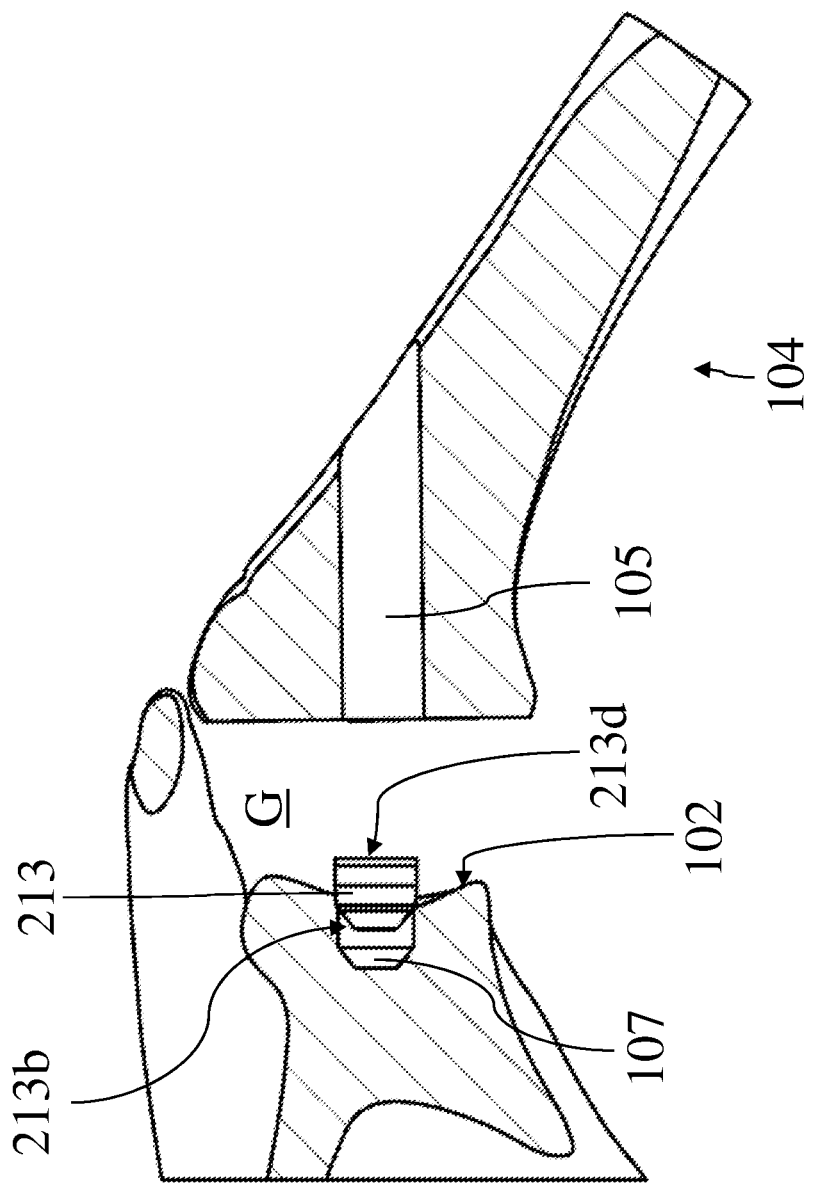
FIG. 9 shows a diagrammatic sectioned view of FIG. 5 with the retractor instrument and the cannulated guide retractor not shown, a peg of a glenoid anchor partially inserted into a peg hole previously made into the glenoid cavity according to the present invention.
Figure 10:
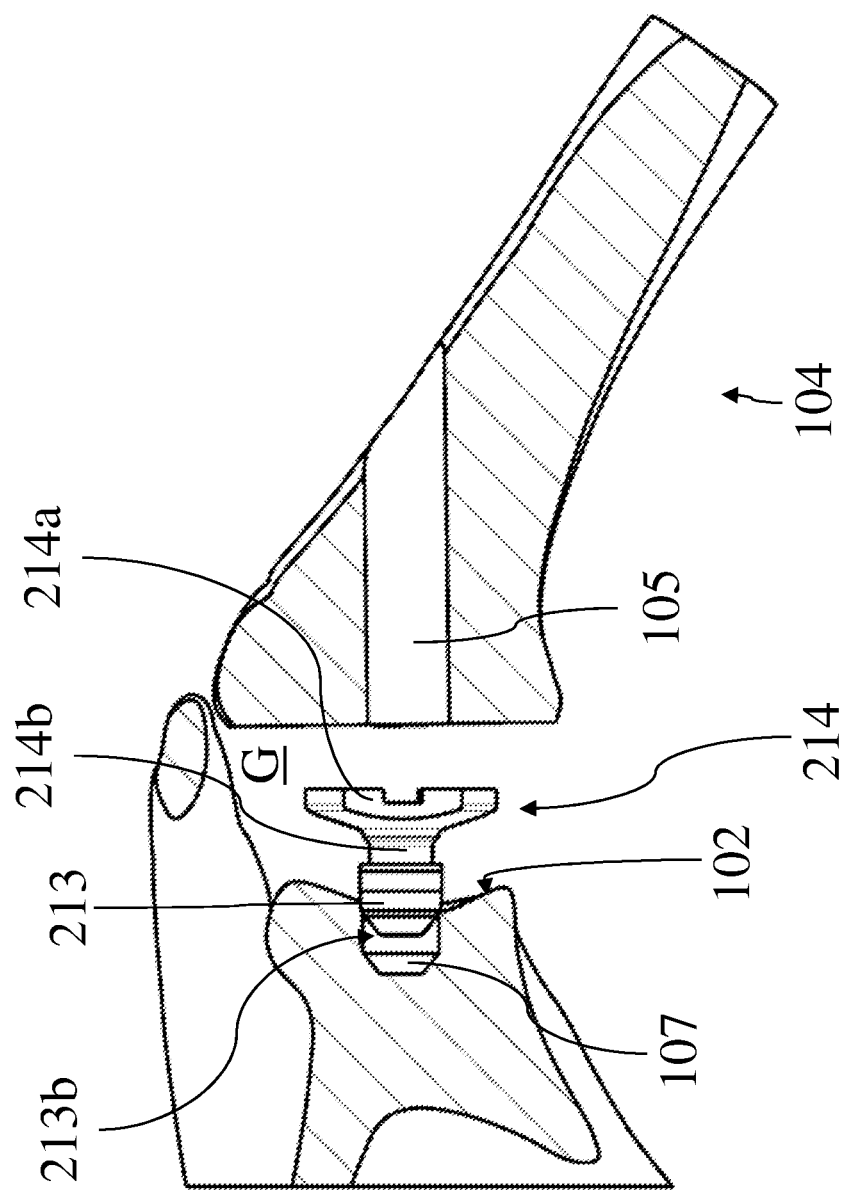
FIG. 10 shows a diagrammatic sectioned view of FIG. 9 with the retractor instrument and the cannulated guide retractor not shown, with a baseplate partially inserted into the peg according to the present invention.

First at all, according to FIG. 9, the peg 213 is provided through the delto-pectoral incision into the gap G and its partially inserted into the peg hole 107 with only the tapered distal end 213b inserted into the peg hole 107.

Then the baseplate 214 is provided through the delto-pectoral incision into the gap G and the lug 214b of the baseplate 214 is partially inserted into the internal cavity 213a of the peg 213, through the proximal opening 213d. In this way, it is defined a conical contact between the lug 214b and the internal cavity 213a; and the baseplate passage 214d is partially concentrically inserted into the internal cavity 213a.

At this stage, it is provided an instrument to press fit the baseplate 214 into the peg 213 and then the peg 213 into the peg hole 107.

Figure 13:
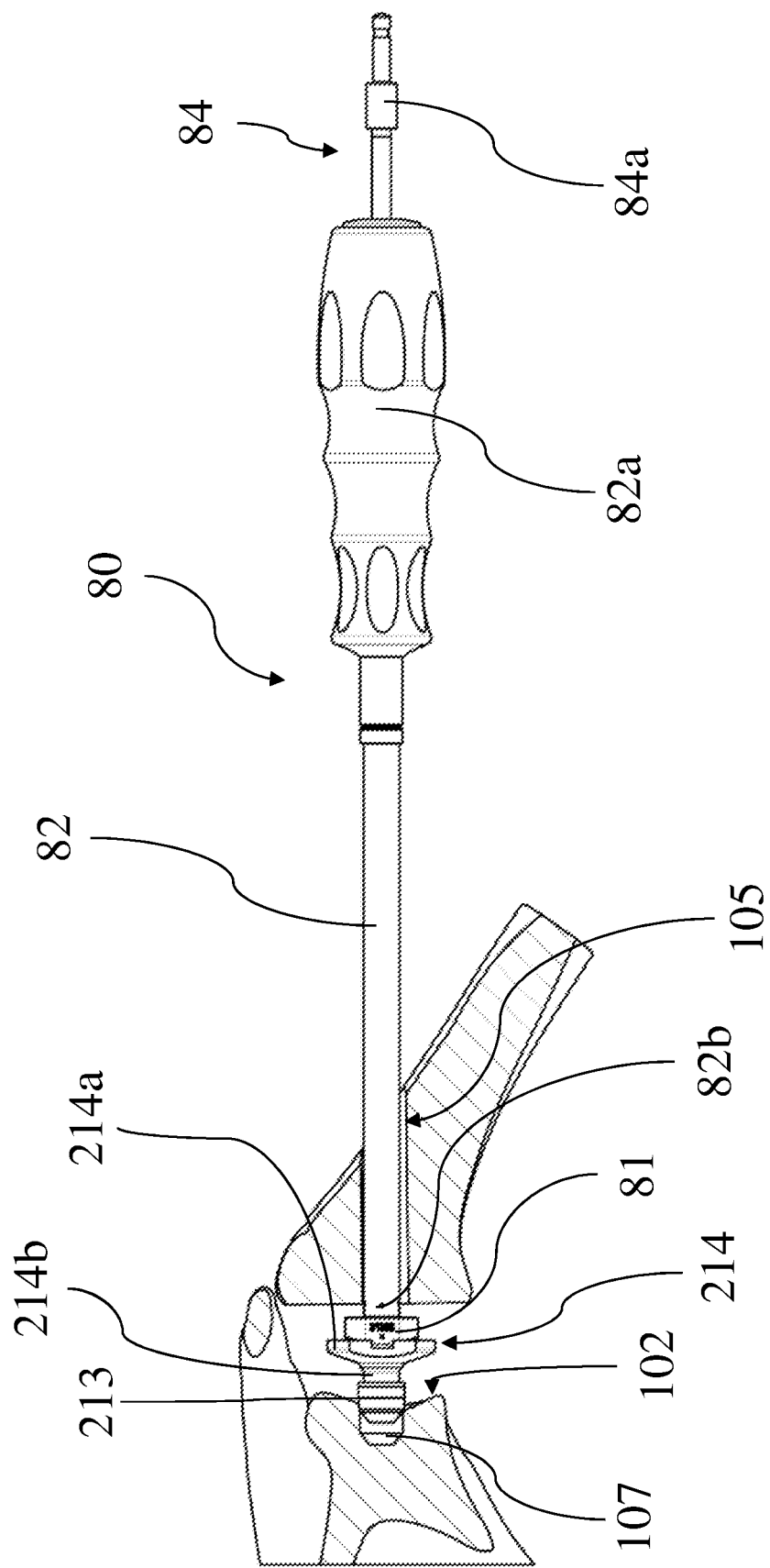
FIG. 13 shows a diagrammatic sectioned view of FIG. 12 with the retractor instrument and the cannulated guide retractor not shown, with a tightening rod inserted through the impactor stem, the impactor head, the baseplate and threaded into the peg according to the present invention.
Figure 14:
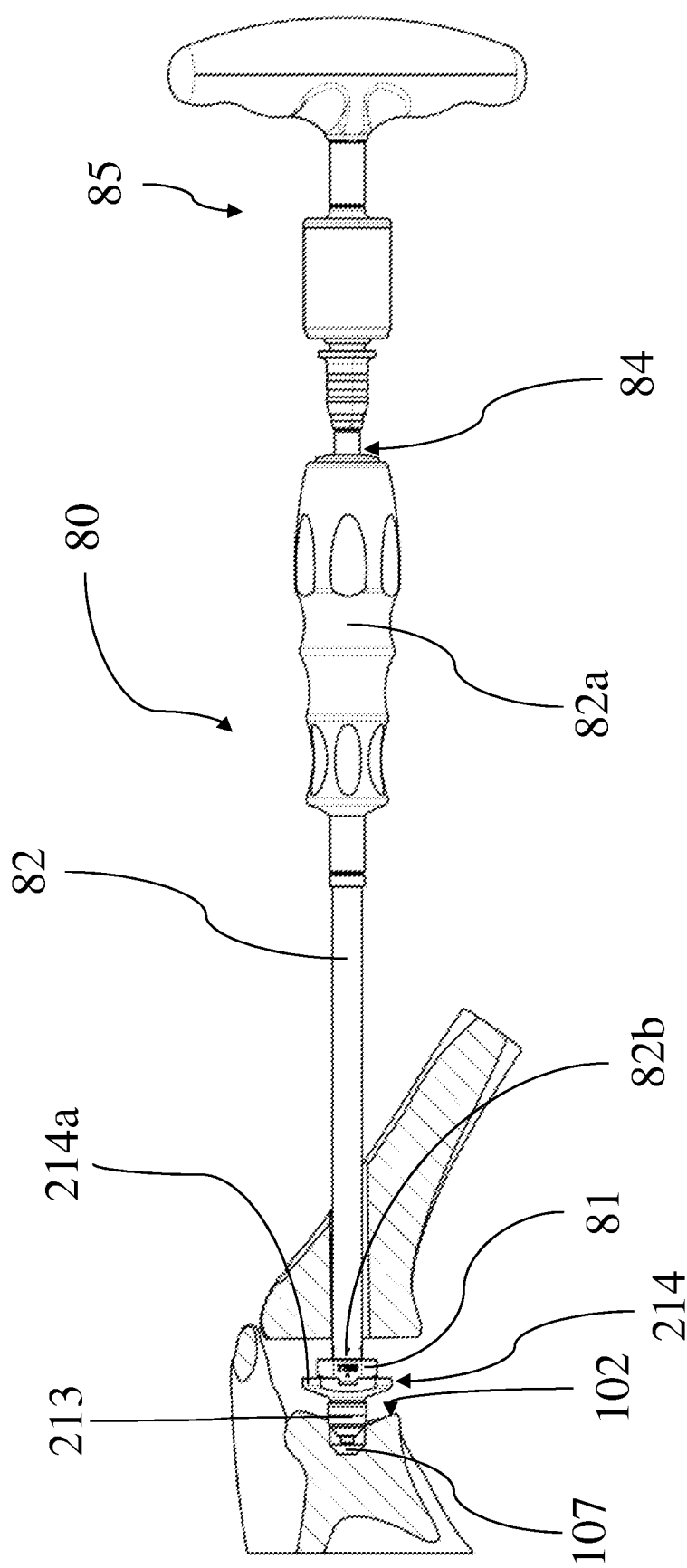
FIG. 14 shows a diagrammatic sectioned view of FIG. 13 with the retractor instrument and the cannulated guide retractor not shown, with a torque wrench coupled to the tightening rod for tightening the tightening rod into the peg of the glenoid anchor for fitting the baseplate into the peg according to the present invention.

For this purpose, it is advantageously provided a cannulated impactor instrument 80, shown in its entirety in FIGS. 13 and 14, comprising a cannulated impactor head 81, an impactor stem 82 with an impactor handle 82a opposite to a head coupling end 82b, and a tightening rod 84.

Figure 11:
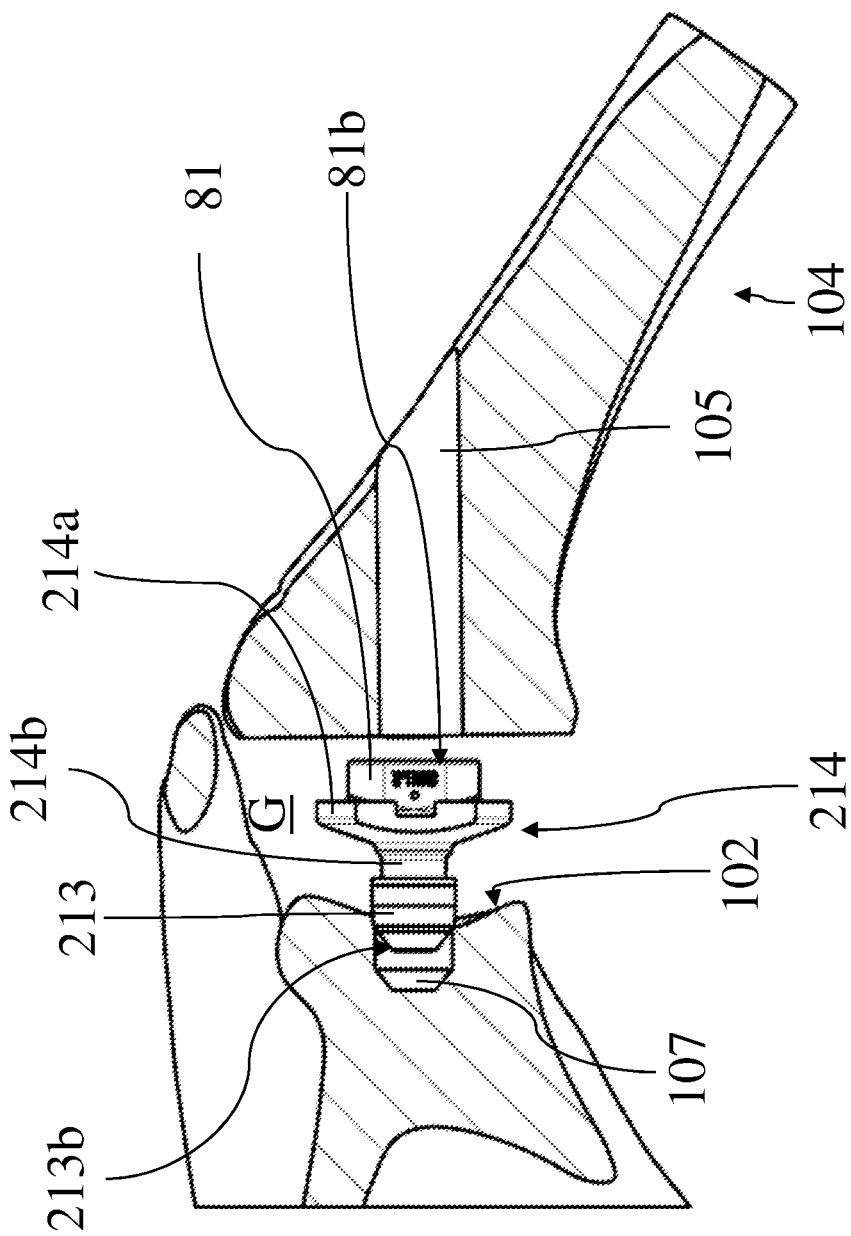
FIG. 11 shows a diagrammatic sectioned view of FIG. 10 with the retractor instrument and the cannulated guide retractor not shown, with a cannulated impactor head abutting against the baseplate according to the present invention.

As shown in FIG. 11, the impactor head 81, introduced through the delto-pectoral incision into the gap G, is placed on the concave surface of the flange 214a of the baseplate 214.

Figure 33:
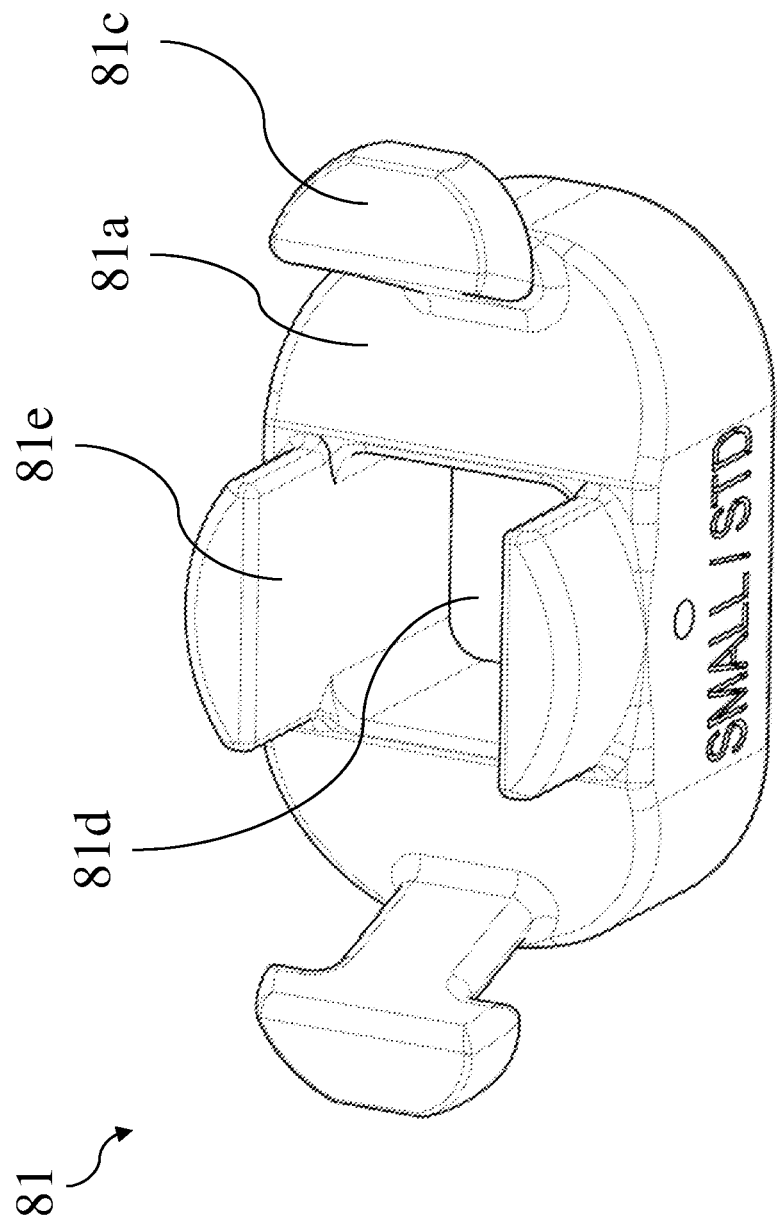
FIG. 33 shows a diagrammatic prospective view of a favorite embodiment of the cannulated impactor head of FIGS. 11-15.

In a preferred embodiment of the impactor head 81, singularly shown in FIG. 33, it has a head facing surface 81a adapted to face the concave surface of the flange 214a opposite to a coupling surface 81b wherein its formed a coupling seat for coupling the head coupling end 82b of the impactor stem 82. The impactor head 81 further comprises an impactor head guide passage 81*d* longitudinally extending therethrough it.

Preferably, protrusions 81*c*, 81*e* extend from the head facing surface 81*a*.

In particular, first protrusions 81*c* are adapted to be inserted into the baseplate holes 214*c* for aligning the impactor head guide passage 81*d* with the baseplate passage 214*d*.

Second protrusions 81*e* are substantially an extension of two side walls that delimit the impactor head guide passage 81*d*. Said second protrusions 81*e* are adapted to abut against a counterbore 214*e* that surrounds the inlet of the baseplate passage 214*d*.

Figure 34:
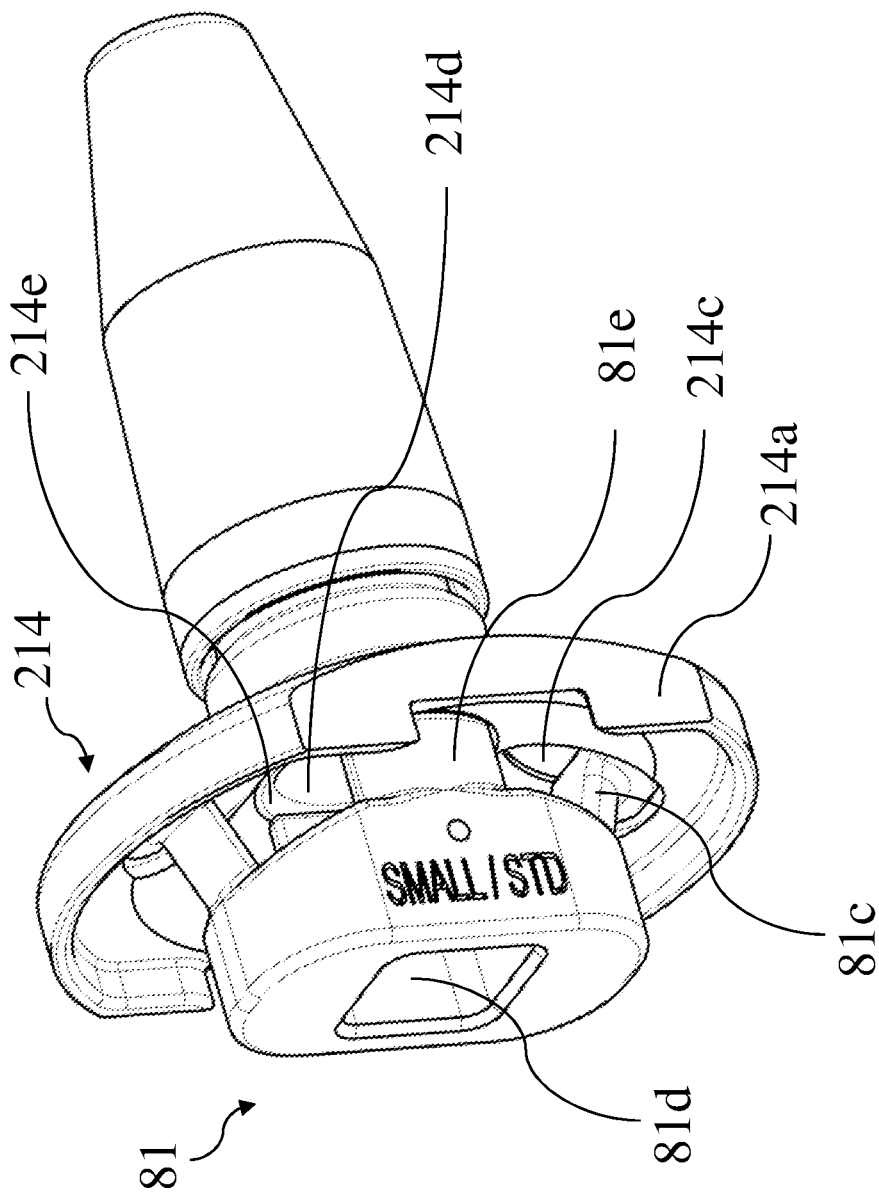
FIG. 34 shows a diagrammatic prospective view of the cannulated impactor head of FIG. 33 during the coupling with the baseplate of the glenoid anchor.

Thus, as shown in FIG. 34, when the impactor head 81 is placed on the concave surface of the flange 214*a*, first protrusion 81*c* are inserted into the relative baseplate holes 214*c* blocking the relative rotations between the impactor head 82 and the baseplate 214, and the second protrusions 81*e* abut against the counterbore 214*e*

Figure 12:
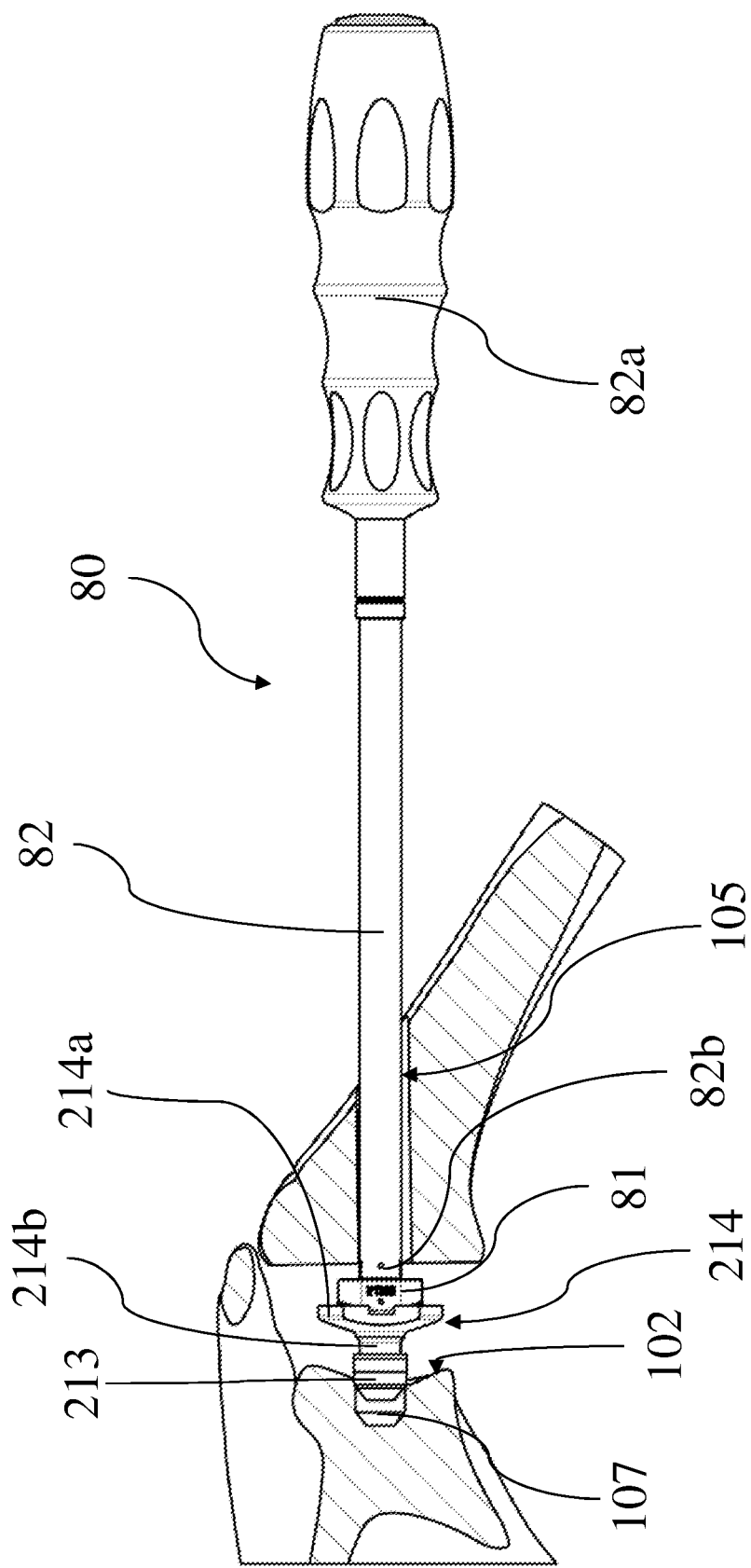
FIG. 12 shows a diagrammatic sectioned view of FIG. 11 with the retractor instrument and the cannulated guide retractor not shown, with an impactor stem inserted through the trans-humeral hole with a free end coupling the impactor head according to the present invention.

When the impactor head 81 is in place, the head coupling end 82*b* of the impactor stem 82 is introduced into the gap G through the trans-deltoid incision and the cannulated guide retractor passage of the cannulated guide retractor 20 and coupled with the coupling seat of the impactor head 82, as shown in FIG. 12.

Figure 27:
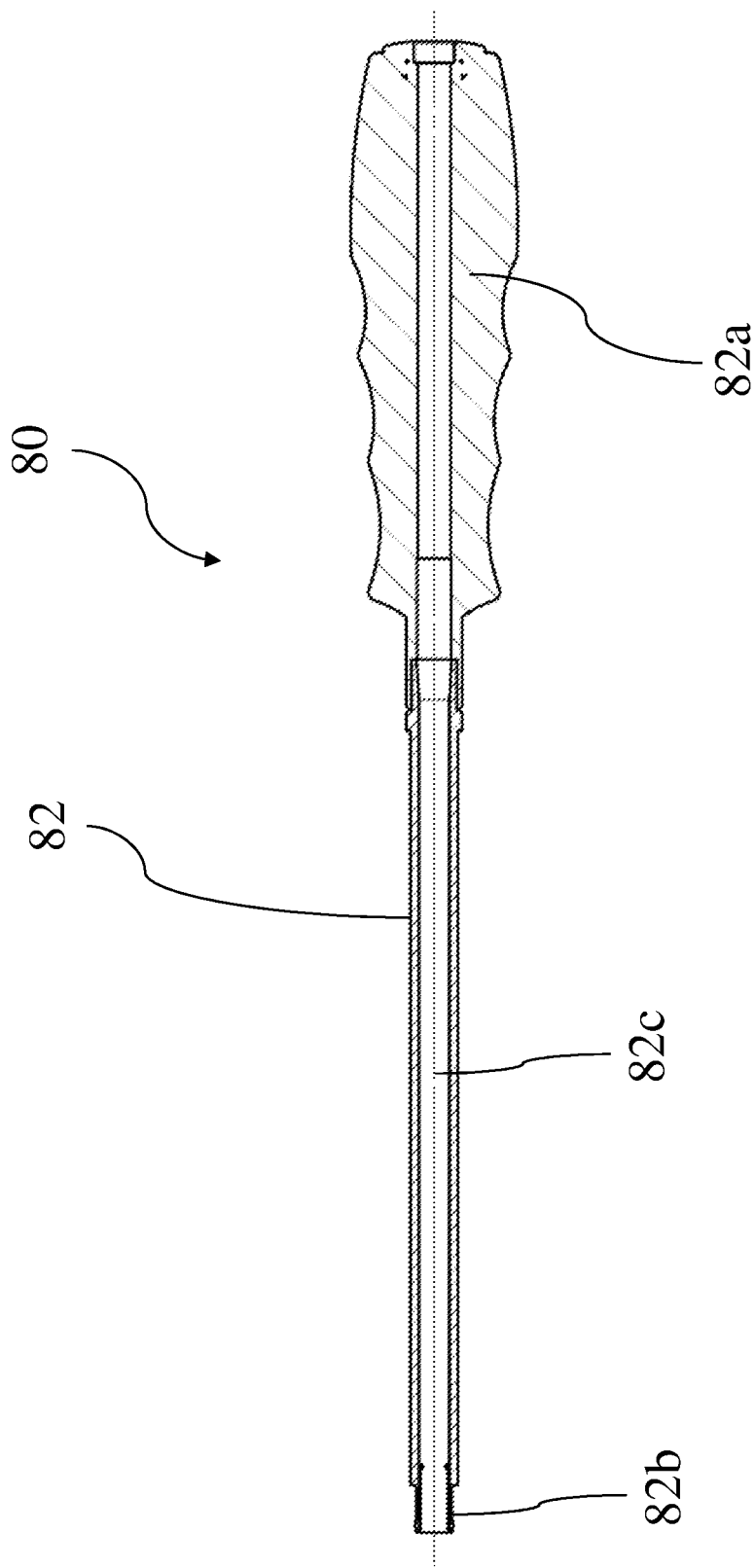
FIG. 27 shows a diagrammatic longitudinal sectioned view of the impactor stem of FIGS. 12-15.

As shown in FIG. 27, the impactor stem 82 further comprises an impactor stem guide passage 82*c* longitudinally extending along all its length from the impactor handle 82*a* to the head coupling end 82*b*. When the head coupling end 82*b* is coupled with the impactor head 81, the impactor stem guide passage 82*c* communicates with the impactor head guide passage 81*d*. In this way, a unique insertion passage is provided extending through the impactor stem 82 and the impactor head 81 of the cannulated impactor instrument 80 and the baseplate 214 and the peg 213 of the glenoid anchor 211. In particular, the unique insertion passage is consequentially defined by the impactor stem guide passage 82*c* and the impactor head guide passage 81*d*, the baseplate passage 214*d* and the internal cavity 102.

Moving to FIG. 13, when the impactor stem 82 is in place, the tightening rod 84 is provided into said unique passage.

In a preferred embodiment of the tightening rod 84, it comprises two opposite ends: a distal rod threaded end and a proximal rod coupling end 84*a* shaped to rotatably coupling a torque wrench 85.

The rod threaded end is consequentially provided through the impactor stem guide passage 82*c*, the impactor head guide passage 81*d*, the baseplate passage 214*d* and the internal cavity 213*a* of the peg 213 until it is threaded into the open hole 213*c* of the peg 213. The rod coupling end 84*a* is leaved outside of the impactor stem 82.

When the cannulated impactor instrument 80 is in place, as shown in FIG. 13, a torque wrench 85 is coupled with the rod coupling end 84*a* of the tightening rod 84.

Using the impactor stem 82 as counter torque, for example holding the impactor handle 82*a*, the rod threaded end is tight into the open hole 213*c* of the peg 213 applying a predetermined torque by means of the torque wrench 85.

Obviously, the person skilled in the art will understand that the controlled tightening of the rod threaded end into the open hole 213*c* determines the interference conical fitting of the lug 214*b* of the baseplate 214 into the internal cavity 213*a* of the peg 213. FIG. 14 shows the lug 241*b* and the peg 13 in a coupled configuration defining the glenoid anchor 211.

When the glenoid anchor 211 is assembled, the torque wrench 85 is detached, the rod threaded end is unscrewed and the tightening rod 84 extracted from the impactor stem 82.

Figure 15:
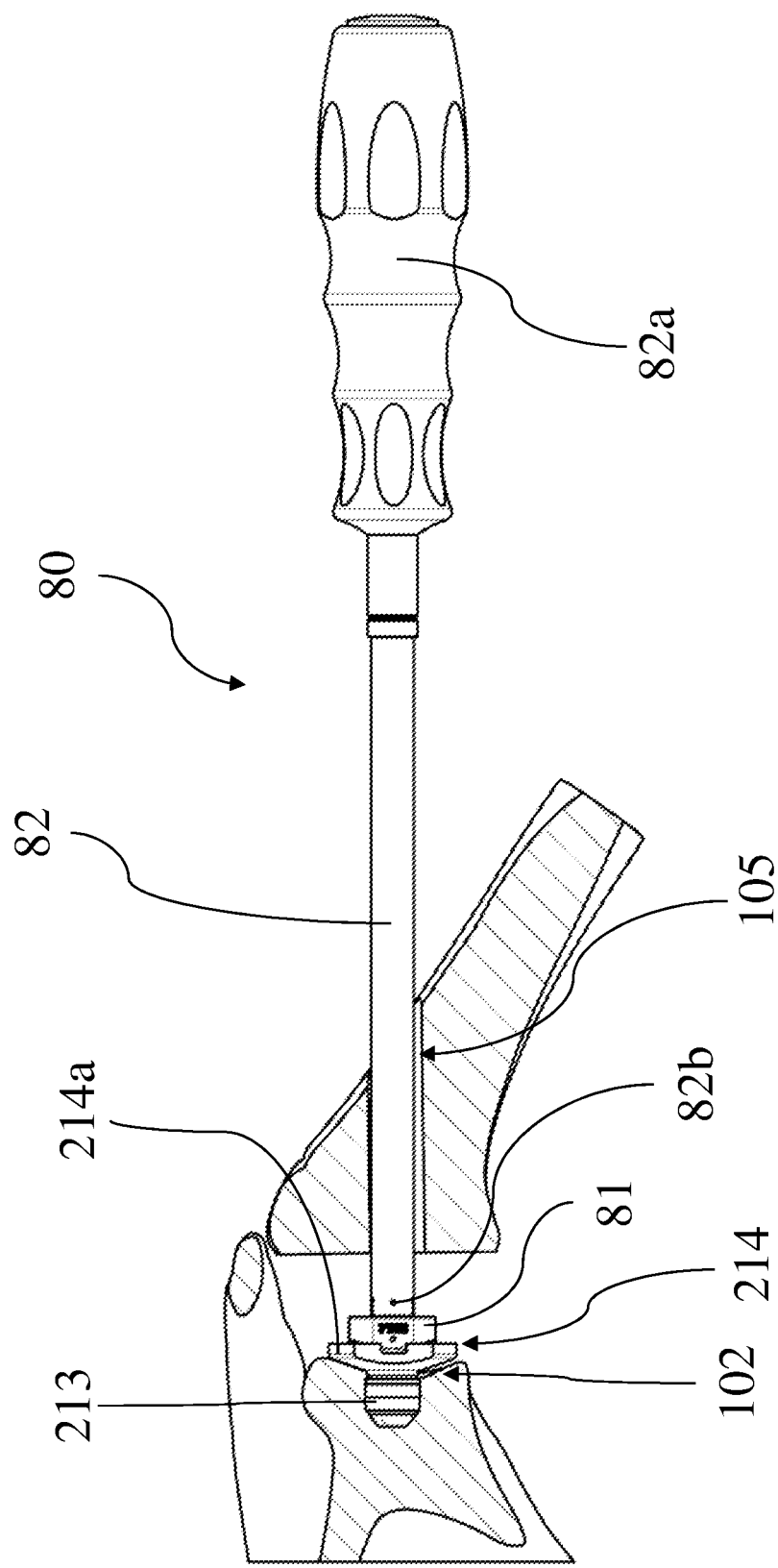
FIG. 15 shows a diagrammatic sectioned view of FIG. 14 with the retractor instrument and the cannulated guide retractor not shown, with the tightening rod extracted from the impactor stem and the peg of the assembled glenoid anchor inserted into the peg hole by pushing the impactor stem according to the present invention.

At this stage, as shown in FIG. 15, the peg 213 of the glenoid anchor 211 is completely inserted into the peg hole 107 abutting the convex surface of the baseplate 214 against the glenoid cavity 102. Obviously, the person skilled in the art will understand that, it is achieved medially pushing the impactor handle 82*a* in the direction of the glenoid cavity 102.

After that, the impactor head 81 and the head coupling end 82*b* of the impactor stem 82 are decoupled each other, the impactor stem 82 is extracted through the trans-deltoid incision and the impactor head 81 is extracted through the delto-pectoral incision.

The flange 214*a* of the baseplate 214 is preferably fixed to the glenoid cavity 102 by means of bone screws inserted into the baseplate hole 214*c*.

Figure 16:
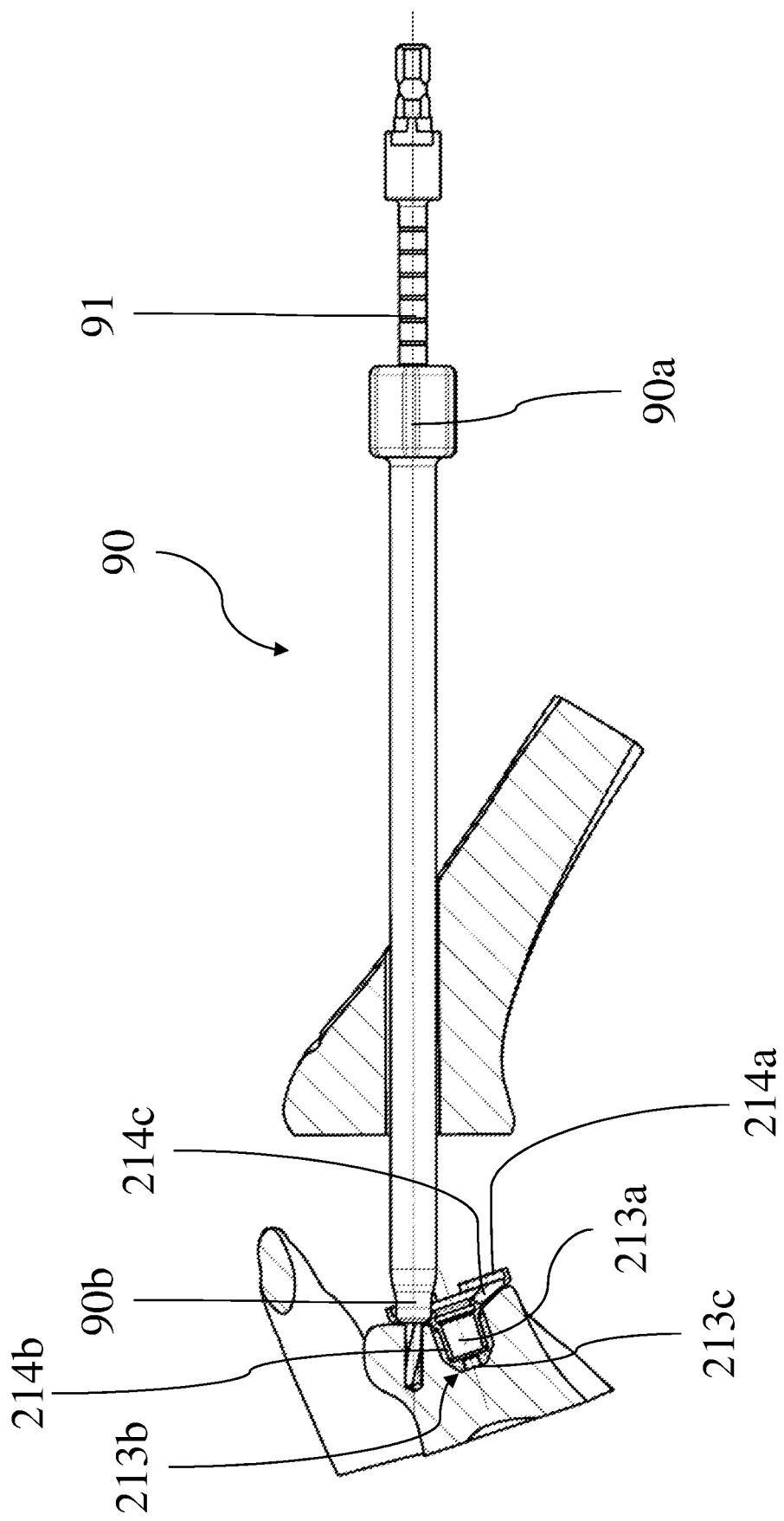
FIG. 16 shows a diagrammatic sectioned view of FIG. 15 with the retractor instrument and the cannulated guide retractor not shown, but with a drill bit guide inserted through the trans-humeral hole into a baseplate hole for bone screw, and a drill bit inserted through the drill bit guide piercing the bone underneath the baseplate hole according to the present infection.

As shown in FIG. 16, the trans-deltoid access could be also used to drill the bone underneath the baseplate holes 214*c* to obtain holes for the screws insertion.

Figure 28:
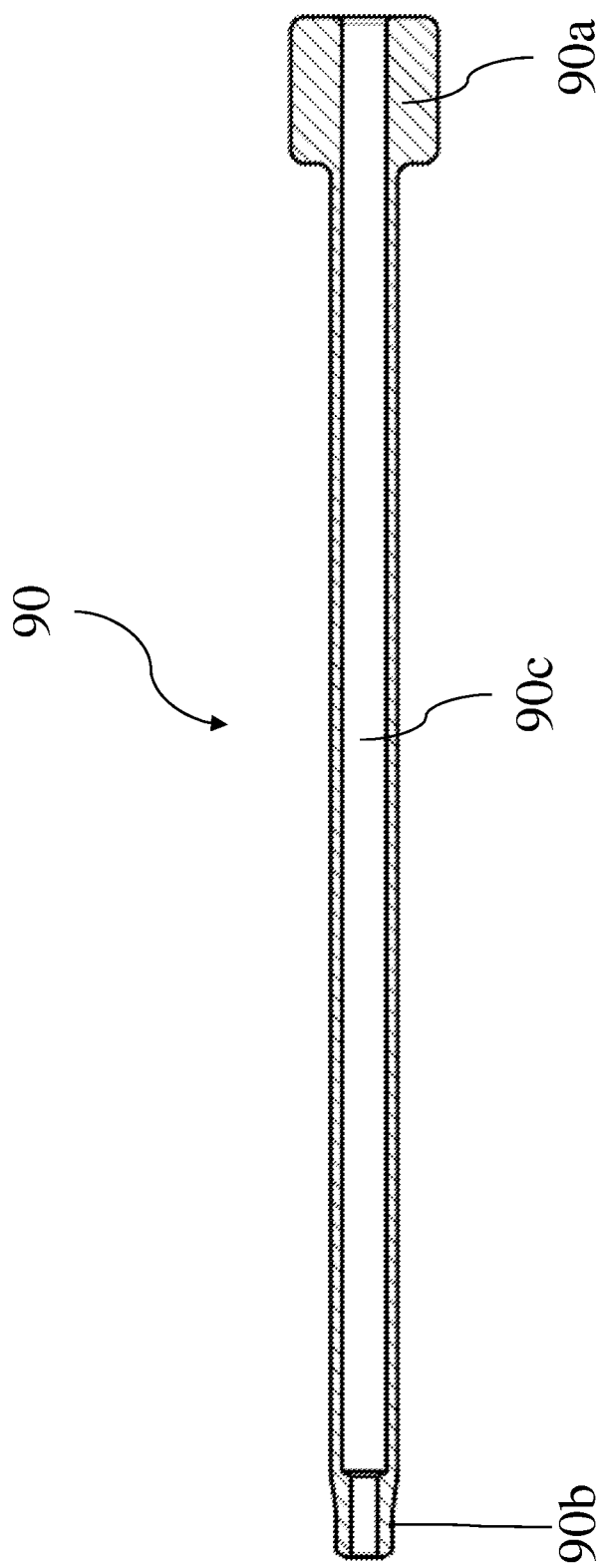
FIG. 28 shows a diagrammatic longitudinal sectioned view of the drill bit guide of FIG. 16.

To do that, it is for example provided a drill bit guide 90 and a screw hole drill bit 91. A favorite embodiment of the drill bit guide 90 shown in FIGS. 16 and 28, has a substantially tubular shape with a drill bit guide passage 90*c* therethrough that extends from a proximal insertion end 90*a* to baseplate hole engaging end 90*b*.

The baseplate hole engaging end 90*b* of the drill bit guide 90 is introduced into the gap G through the trans-deltoid incision and the cannulated guide retractor passage of the cannulated guide retractor 20 leaving the insertion end 90*a* outside of the patient body and seating the baseplate hole engaging end 90*b* into one of the baseplate holes 214*c*. The drill bit 91 is then inserted through the insertion end 90*a* and the drill bit guide passage 90*c*, into the baseplate hole engaging end 90*b*, and operated in order to piercing the bone beneath the baseplate hole 214*c*.

The bone screws could then be positioned through the baseplate hole 214*c*.

Figure 20:
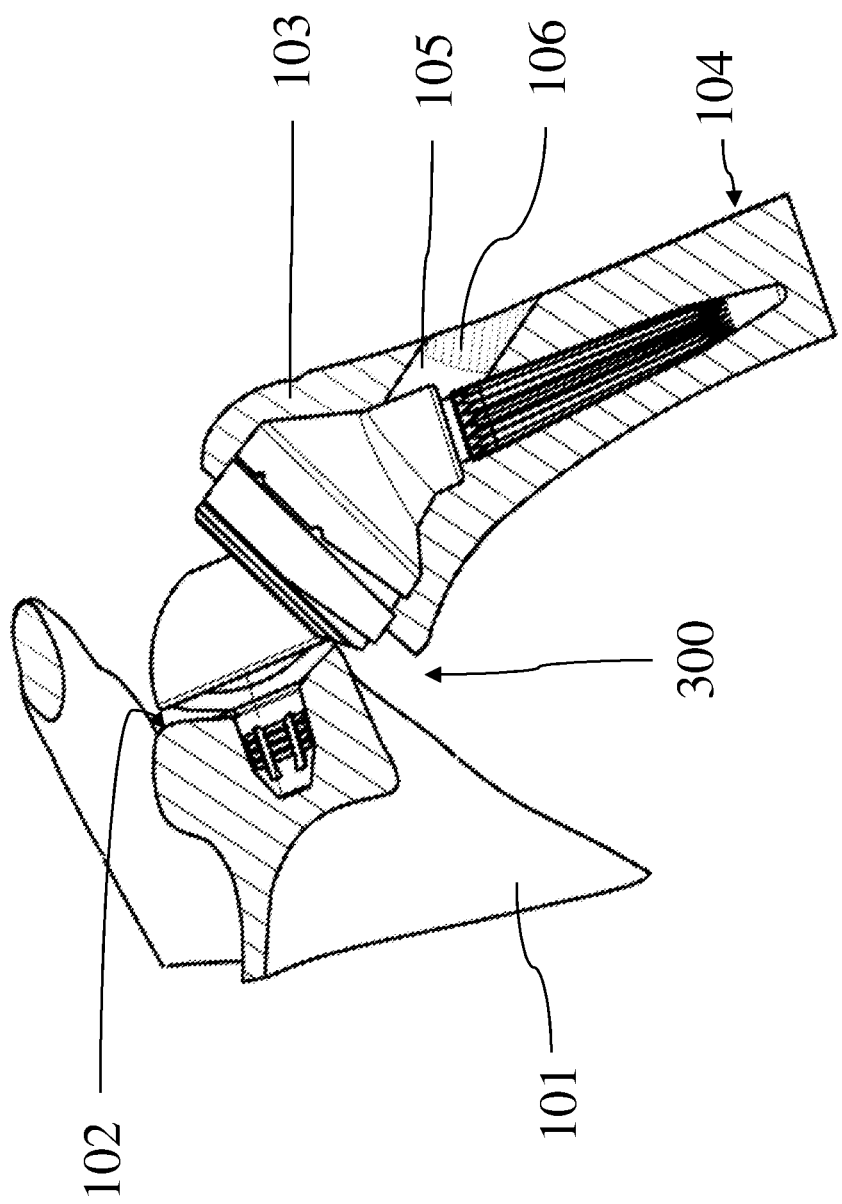
FIG. 20 shows a diagrammatic partially sectioned view taken on a frontal plane of an exemplary reverse total shoulder prosthesis with a glenoid component implanted in the shoulder joint of FIG. 1 by means of the method and the instruments according the present invention.

FIG. 20 shows an exemplary reverse total shoulder prosthesis 300 with a glenoid component implanted in the shoulder joint 100 of FIG. 1 by means of the method and the instruments according to the present invention.

The surgical method and the claimed products according to the present invention solves the technical problem and accomplish many advantages.

First of all, the surgery method according to the present invention is less invasive than the known surgery method because it does not need to expose the glenoid cavity to be machined and implant the glenoid component of the shoulder prosthesis.

This approach advantageously allows to preserve numerous anatomical structures that concur to stabilize the shoulder joint, in particular the subscapularis muscle.

As the skilled in the art will surely appreciate, the method according to the present invention contributes to reduce the after-surgery pain and the duration of the convalesce allowing the patient to come back sooner to his normal daily life. Said approach essentially consists in providing both a delto-pectoral access and a lateral or trans-deltoid access for the insertion of surgical instruments used for shaping the bone of the glenoid cavity and implanting the glenoid anchor. The surgical instruments advantageously comprise a tool to be inserted through the delto-pectoral access and a stem to be inserted through the lateral access coupling the machining tool. Said lateral access is advantageously provided by a lateral skin and tissues incision and a through hole into the humeral head.

To achieve the objective of the invention, the present invention advantageously provides a retractor instrument inserted through a delto-pectoral access that keeps a predetermined space between the glenoid cavity and humeral head. Unlike the known retractors having a plane continues paddle abutting the anatomical structures, the retractor instrument of the present invention has abutting elements expressly shaped to abut against the humeral head and the scapula allowing to keep free the humeral head top and the glenoid cavity.

In particular, the retractor instrument comprises a flat annular element abutting against the humeral head and a U-shaped element inferiorly surrounding the coracoid process.

The abutting elements of the retractor instrument could be formed in other shapes that allows to keep free the glenoid cavity and the humeral head top. For example, the first abutting element could have a C-shape or other shapes partially surrounding the trans-humeral hole. The second abutting element could instead abut against the acromion or at least partially around the borders of the glenoid cavity.

Another instrument according to the present invention that acts a particularly advantageous rule in the method according to the present invention is the cannulated retractor guide. The cannulated retractor guide provides two important functions: (i) keeping retracted the soft tissues that are between the trans-deltoid incision and the humeral head thanks to the tapered shape of its retracting portion, (ii) guiding the insertion of the surgical instruments through the trans-deltoid incision and the trans-humeral hole into the space between the glenoid cavity and humeral head thanks to the tubular shaped insertion portion inserted into the trans-humeral hole and the guide passage extending therethrough the cannulated guide retractor.

Furthermore, the machining of the glenoid cavity according to the surgery method of the present invention advantageously considers the laterally introduction, through the trans-humeral hole, of the machining stem and the frontal introduction, through the delto-pectoral incision, of the machining tool coupled with the relative machining stem into the space between the glenoid cavity and humeral head.

The machining tools according to the present invention advantageously comprising a longitudinally through passage for the insertion of the guidewire and a radial recess extending from one side of the machining tool to the through passage. The radial recess advantageously allows to insert/extract the guidewire into/from the through passage when the guidewire is inserted into the bone. In other word, it is possible to substitute the machining tool without extracting the guidewire and the stem.

The method according to present invention advantageously comprises a step of press fitting a peg and a baseplate of the glenoid anchor, inserted through the delto-pectoral incision, by means of a cannulated impactor instrument.

The impactor instrument advantageously comprising an impactor head, inserted through the delto-pectoral incision, abutting the baseplate and an impactor stem, inserted through the trans-deltoid incision, coupled to the impactor head. A tightening rod is advantageously inserted through an impactor passage provided therethrough the cannulated impactor instrument and the baseplate, until a threaded rod free end is threaded into the peg. The peg and the baseplate could be coupled in a controlled manner using the impactor stem to apply a counter torque and rotating the tightening rod tightening the rod free end.

The method according to the present invention also comprises the step of providing a bone graft from a resected humeral head top that is advantageously used to fill the trans-humeral hole at the end of the prosthesis implant. The bone graft allows to locally increase the bone strength at the previously created bone discontinuity.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "portion", "piece", or "element" when used in the singular can have the dual meaning of a single part or a plurality of parts unless otherwise stated.

As used herein, the following directional terms "medial", "lateral", "frontal", "internal", "external", "proximal", "distal", "sagittal", "coronal", as well as any other similar directional terms refer to those directions of a patient body lying on an operating table according to the standard anatomical terms of location used in the field of human anatomy.

Also, it will be understood that although the terms "first" and "second" may be used herein to describe various components these components should not be limited by these terms. These terms are only used to distinguish one component from another. Thus, for example, a first component discussed above could be termed a second component and vice versa without departing from the teachings of the present invention. The term "coupled" or "coupling", as used herein, encompasses configurations in which an element is directly secured to another element by affixing the element directly to the other element; configurations in which the element is indirectly secured to the other element by affixing the element to the intermediate member(s) which in turn are affixed to the other element; and configurations in which one element is integral with another element, i.e. one element is essentially part of the other element. This definition also applies to words of similar meaning, for example, "connected", "fixed", "fitted", "mount" and their derivatives. Finally, terms of degree such as "substantially", "essentially", "about" and "approximately" as used herein mean an amount of deviation of the modified term such that the end result is not significantly changed.

Obviously, a person skilled in the art may make numerous modifications and variations to the invention described above in order to satisfy particular and specific requirements, all however within the scope of protection of the invention as defined in the following claims.

The invention claimed is:

1. A method for surgical application of a glenoid anchor or a glenoid prosthesis component of a shoulder joint prosthesis, comprising:
   making a delto-pectoral incision providing a delto-pectoral access to a shoulder joint, the shoulder joint comprising a humeral head of a humerus facing a glenoid cavity of a shoulder blade;
   inserting a machining tool in the delto-pectoral access;
   making a trans-deltoid lateral incision providing a trans-deltoid lateral access to the humeral head;
   inserting a stem of a machining instrument in the trans-deltoid lateral access;

mounting the machining tool on the stem of the machining instrument; and machining, with the machining tool, the glenoid cavity.

2. The method according to claim 1 further comprising:

exposing the humeral head dislocating the humerus by an external rotation of the arm;

making a through trans-humeral hole into the humeral head extending in medio-lateral direction;

returning the humeral head facing the glenoid cavity;

providing a retractor instrument introduced through the delto-pectoral access the retractor instrument having an abutting element at least partially abutting against the humeral head and the shoulder blade keeping free the trans-humeral hole and the glenoid cavity;

keeping, with the retractor instrument, a predetermined glenohumeral clearance between the humeral head and the glenoid cavity;

providing the machining tool in the glenohumeral clearance introduced through the delto-pectoral access;

introducing the stem of a machining instrument through the trans-deltoid lateral access and then the trans-humeral hole until a stem free end of the stem reaches the glenohumeral clearance;

mounting the machining tool on the stem free end for machining the glenoid cavity.

3. The method according to claim 2, wherein the step of making a through trans-humeral hole in the humeral head comprises:

providing a guidewire;

providing a cannulated centering device having a centering device guide passage for the guidewire and an abutting portion for abutting against a humeral head top of the humeral head;

abutting the abutting portion against the humeral head top orienting the centering device guide passage in medio-lateral direction;

introducing the guidewire through the centering device guide passage inserting a guidewire tip into the humeral head;

guiding, with the guidewire, a cannulated drill bit; and drilling the humeral head by the cannulated drill bit using the guidewire as guide.

4. The method according to claim 3 further comprising resecting the humeral head top.

5. The method according to claim 4, wherein before the step of inserting the stem of the machining instrument through the trans-deltoid lateral access the method comprises a step of:

providing a cannulated guide retractor introduced through the trans-deltoid lateral access; the cannulated guide retractor having an instrument guide passage therethrough connecting the trans-deltoid lateral incision to the trans-humeral hole;

wherein the step of introducing the stem of the machining instrument comprises introducing the stem through the instrument guide passage of the cannulated guide retractor.

6. The method according to claim 5, wherein the cannulated guide retractor comprises a retracting portion, and the method further comprising:

providing a cannulated guide retractor; and retracting soft tissues located between the trans-deltoid lateral incision and the trans-humeral hole by the retracting portion of the cannulated guide retractor.

7. The method according to claim 6, wherein the cannulated guide retractor comprises an insertion portion, and the method further comprising:

at least partially inserting the insertion portion into the trans-humeral hole;

passing the insertion portion through the instrument guide passage; and at least partially introducing the insertion portion into the trans-humeral hole by a cannulated guide retractor.

8. The method according to claim 7, wherein the machining tool is a cannulated machining tool having a longitudinal machining tool passage therethrough; and before the step of inserting the stem of the machining instrument, the method comprises:

introducing the guidewire through the trans-deltoid lateral access, the instrument guide passage and then the longitudinal machining tool passage until the guidewire tip is inserted into the glenoid cavity; and wherein the step of introducing the stem of the machining instrument comprises using the guidewire to guide the stem insertion.

9. The method according to claim 8, wherein the machining tool comprises a radial slot passing from an outer side of the machining tool to the longitudinal machining tool passage; and the method further comprises:

decoupling the stem from the machining tool; and extracting the machining tool by passing the guidewire through the radial slot.

10. The method according to claim 9, wherein the machining tool is a milling tool for milling the glenoid cavity exposing the subchondral bone; and the method further comprises:

providing a cannulated reamer into the glenohumeral clearance through the delto-pectoral access;

making a hole, with the cannulated reamer, into the glenoid cavity for a peg of the glenoid anchor; the cannulated reamer having a longitudinal reamer passage therethrough and a reamer radial slot extending from an outer side of the reamer to the longitudinal reamer passage;

transversally inserting the guidewire into the longitudinal reamer passage through the reamer radial slot;

mounting the reamer on the stem free end; and making the peg hole into the glenoid cavity.

11. The method according to claim 10 further comprising:

providing a glenoid anchor comprising a peg extending from a baseplate;

partially inserting the peg into the peg hole;

providing an impactor comprising an impactor stem and an impactor head;

abutting the impactor head inserted through the delto-pectoral access against the baseplate;

inserting the impactor stem through the trans-deltoid lateral access and the instrument guide passage until an impactor stem free end reaches the glenohumeral clearance;

mounting the impactor head on the impactor stem free end; and fitting the peg into the peg hole medially pushing the impactor in direction of the glenoid cavity.

12. The method according to claim 11, wherein the peg and the baseplate are two separated pieces; the baseplate having a lug adapted to be inserted into an internal cavity of the peg; the baseplate having a baseplate passage extending through the lug; the impactor stem having a impactor stem guide passage therethrough and the impactor head having a impactor head guide passage therethrough; the impactor stem guide passage and the impactor head guide passage being in communication when the impactor head is mounted to the impactor stem free end; before providing an impactor, the method further comprises partially inserting the lug into the peg; and before the step of fitting the peg into the peg hole, the method comprises:
- providing a tightening rod having a rod threaded end and a rod coupling end;
- inserting the rod threaded end through the impactor stem guide passage, the impactor head guide passage and the baseplate passage;
- threading the rod threaded end into an internal thread of the internal cavity of the peg leaving the rod coupling end outside of the impactor stem;
- providing a torque wrench mounted to the rod coupling end;
- fitting the lug of the baseplate into the peg tightening the rod threaded end of the tightening rod into the peg; wherein the tightening of the rod threaded end is achieved applying a torque to the rod coupling end with the torque wrench using the impactor has counter torque.

13. The method according to claim 12, wherein the baseplate comprises a through baseplate hole to fasten the baseplate to the glenoid cavity by bone screws; and the method further comprises making a screw hole into the glenoid cavity for the insertion of the bone screws inserting a drill bit through the trans-deltoid lateral access, the instrument guide passage and then the baseplate hole.

14. The method according to claim 13 further comprising:
- providing a bone graft from the resected humeral head top; and
- introducing the bone graft into the through trans-humeral hole.

* * * * *